United States Patent
Griffin

(10) Patent No.: US 11,471,162 B2
(45) Date of Patent: Oct. 18, 2022

(54) OCCLUSION DEVICE

(71) Applicant: Cerus Endovascular Limited, Oxford (GB)

(72) Inventor: Stephen Griffin, San Jose, CA (US)

(73) Assignee: Cerus Endovascular Limited, Oxford (GB)

(\*) Notice: Subject to any disclaimer, the term of this patent is extended or adjusted under 35 U.S.C. 154(b) by 677 days.

(21) Appl. No.: 16/407,957

(22) Filed: May 9, 2019

(65) Prior Publication Data

US 2019/0269414 A1    Sep. 5, 2019

Related U.S. Application Data

(63) Continuation of application No. 15/372,128, filed on Dec. 7, 2016, now Pat. No. 10,285,711.

(60) Provisional application No. 62/264,171, filed on Dec. 7, 2015.

(51) Int. Cl.
*A61B 17/12* (2006.01)
*A61B 17/00* (2006.01)
*A61B 90/00* (2016.01)

(52) U.S. Cl.
CPC .... *A61B 17/12172* (2013.01); *A61B 17/0057* (2013.01); *A61B 17/12113* (2013.01); *A61B 17/12163* (2013.01); *A61B 2017/00632* (2013.01); *A61B 2017/00862* (2013.01); *A61B 2017/00867* (2013.01); *A61B 2017/12063* (2013.01); *A61B 2090/3966* (2016.02)

(58) Field of Classification Search
CPC .......... A61B 17/12172; A61B 17/0057; A61B 17/12113; A61B 17/12163; A61B 2017/00632
See application file for complete search history.

(56) References Cited

U.S. PATENT DOCUMENTS

| | | | |
|---|---|---|---|
| 2,849,002 | A | 8/1958 | Oddo |
| 3,480,017 | A | 11/1969 | Shute |
| 4,364,392 | A | 12/1982 | Strother et al. |
| 4,395,806 | A | 8/1983 | Wonder et al. |
| 4,545,367 | A | 10/1985 | Tucci |
| 4,836,204 | A | 6/1989 | Landymore et al. |
| 4,991,602 | A | 2/1991 | Amplatz et al. |

(Continued)

FOREIGN PATENT DOCUMENTS

| | | |
|---|---|---|
| CA | 2946078 | 11/2015 |
| CN | 102940514 | 3/2013 |

(Continued)

OTHER PUBLICATIONS

US 9,034,010 B2, 05/2015, Amin (withdrawn)

(Continued)

*Primary Examiner* — Ashley L Fishback
(74) *Attorney, Agent, or Firm* — Fish & Richardson P.C.

(57) ABSTRACT

Provided herein is an occlusion device for implantation into a body lumen or aneurysm comprising, a continuous compressible mesh structure comprising axial mesh carriages configured end to end, wherein each end of each carriage is a pinch point in the continuous mesh structure. Also provided herein is a kit comprising the occlusion device disclosed herein and a means for delivery thereof. Methods of manufacture and use of the occlusion device are also disclosed.

12 Claims, 6 Drawing Sheets

(56) References Cited

U.S. PATENT DOCUMENTS

| | | |
|---|---|---|
| 5,002,556 A | 3/1991 | Ishida et al. |
| 5,025,060 A | 6/1991 | Yabuta et al. |
| 5,065,772 A | 11/1991 | Cox, Jr. |
| 5,067,489 A | 11/1991 | Lind |
| 5,122,136 A | 6/1992 | Guglielmi et al. |
| 5,192,301 A | 3/1993 | Kamiya et al. |
| 5,423,829 A | 6/1995 | Pham et al. |
| 5,496,277 A | 3/1996 | Termin et al. |
| 5,624,449 A | 4/1997 | Pham et al. |
| 5,733,294 A | 3/1998 | Forber et al. |
| 5,891,128 A | 4/1999 | Gia et al. |
| 5,928,260 A | 7/1999 | Chin et al. |
| 6,007,573 A | 12/1999 | Wallace et al. |
| 6,024,756 A | 2/2000 | Pham |
| 6,080,191 A | 6/2000 | Thaler |
| 6,096,021 A | 8/2000 | Helm et al. |
| 6,113,609 A | 9/2000 | Adams |
| 6,123,714 A | 9/2000 | Gia et al. |
| 6,152,144 A | 11/2000 | Lesh et al. |
| 6,168,579 B1 | 1/2001 | Tsugita |
| 6,168,622 B1 | 1/2001 | Mazzocchi |
| 6,221,086 B1 | 4/2001 | Forber |
| 6,270,515 B1 | 8/2001 | Linden et al. |
| 6,315,787 B1 | 11/2001 | Tsugita et al. |
| 6,334,048 B1 | 12/2001 | Edvardsson et al. |
| 6,419,686 B1 | 7/2002 | McLeod et al. |
| 6,454,780 B1 | 9/2002 | Wallace |
| 6,463,317 B1 | 10/2002 | Kucharczvk et al. |
| 6,506,204 B2 | 1/2003 | Mazzocchi |
| 6,527,919 B1 | 3/2003 | Roth |
| 6,547,804 B2 | 4/2003 | Porter et al. |
| 6,551,303 B1 | 4/2003 | Tassel et al. |
| 6,569,190 B2 | 5/2003 | Whalen, II et al. |
| 6,589,230 B2 | 7/2003 | Gia et al. |
| 6,589,256 B2 | 7/2003 | Forber |
| 6,605,102 B1 | 8/2003 | Mazzocchi et al. |
| 6,620,152 B2 | 9/2003 | Guglielmi |
| 6,663,068 B2 | 12/2003 | Huang |
| 6,669,719 B2 | 12/2003 | Wallace et al. |
| 6,669,721 B1 | 12/2003 | Bose et al. |
| 6,689,159 B2 | 2/2004 | Lau et al. |
| 6,780,196 B2 | 8/2004 | Chin et al. |
| 6,811,560 B2 | 11/2004 | Jones |
| 6,833,003 B2 | 12/2004 | Jones et al. |
| 6,855,154 B2 | 2/2005 | Abdel-Gawwad |
| 6,949,116 B2 | 9/2005 | Solvmar et al. |
| 6,953,472 B2 | 10/2005 | Palmer |
| 7,044,134 B2 | 5/2006 | Khairkhahan et al. |
| 7,093,527 B2 | 8/2006 | Rapaport et al. |
| 7,128,073 B1 | 10/2006 | Burg et al. |
| 7,128,736 B1 | 10/2006 | Abrams et al. |
| 7,152,605 B2 | 12/2006 | Khairkhahan et al. |
| 7,195,636 B2 | 3/2007 | Avellanet et al. |
| 7,229,454 B2 | 6/2007 | Tran et al. |
| 7,229,461 B2 | 6/2007 | Chin et al. |
| 7,232,461 B2 | 6/2007 | Ramer |
| 7,306,622 B2 | 12/2007 | Jones |
| 7,371,249 B2 | 5/2008 | Douk et al. |
| 7,410,482 B2 | 8/2008 | Murphey et al. |
| 7,572,288 B2 | 8/2009 | Cox |
| 7,597,704 B2 | 10/2009 | Frazier et al. |
| 7,695,488 B2 | 4/2010 | Berenstein et al. |
| 7,713,264 B2 | 5/2010 | Murphy |
| 7,722,641 B2 | 5/2010 | Burg et al. |
| 7,744,652 B2 | 6/2010 | Morsi |
| 7,828,818 B2 | 11/2010 | Zang et al. |
| 7,892,254 B2 | 2/2011 | Klint |
| 8,034,061 B2 | 10/2011 | Amplatz et al. |
| 8,066,757 B2 | 11/2011 | Ferrera |
| 8,075,585 B2 | 12/2011 | Lee et al. |
| 8,080,032 B2 | 12/2011 | Burg et al. |
| 8,088,140 B2 | 1/2012 | Ferrera |
| 8,142,456 B2 | 3/2012 | Rosqueta et al. |
| 8,221,483 B2 | 7/2012 | Ford et al. |
| 8,252,040 B2 | 8/2012 | Cox |
| 8,261,648 B1 | 9/2012 | Marchand et al. |
| 8,262,692 B2 | 9/2012 | Rudakov |
| 8,267,923 B2 | 9/2012 | Murphy |
| 8,361,106 B2 | 1/2013 | Solar et al. |
| 8,361,138 B2 | 1/2013 | Adams |
| 8,372,114 B2 | 2/2013 | Hines |
| 8,398,671 B2 | 3/2013 | Chen |
| 8,430,012 B1 | 4/2013 | Marchand et al. |
| 8,454,633 B2 | 6/2013 | Amplatz et al. |
| 8,470,013 B2 | 6/2013 | Duggal et al. |
| 8,500,751 B2 | 8/2013 | Rudakov et al. |
| 8,523,897 B2 | 9/2013 | Burg et al. |
| 8,535,343 B2 | 9/2013 | Burg et al. |
| 8,545,514 B2 | 10/2013 | Ferrera |
| 8,562,667 B2 | 10/2013 | Cox |
| 8,574,262 B2 | 11/2013 | Ferrera |
| 8,585,713 B2 | 11/2013 | Ferrera |
| 8,597,320 B2 | 12/2013 | Sepetka |
| 8,663,273 B2 | 3/2014 | Airkhahan |
| 8,696,701 B2 | 4/2014 | Becking |
| 8,715,312 B2 | 5/2014 | Burke |
| 8,715,316 B1 | 5/2014 | Janardhan et al. |
| 8,747,453 B2 | 6/2014 | Amplatz |
| 8,771,294 B2 | 7/2014 | Sepetka |
| 8,834,519 B2 | 9/2014 | Van Der Burg |
| 8,926,680 B2 | 1/2015 | Ferrera |
| 8,945,172 B2 | 2/2015 | Ferrera |
| 9,034,054 B2 | 5/2015 | Gerberding |
| 9,039,724 B2 | 5/2015 | Amplatz et al. |
| 9,060,077 B2 | 6/2015 | Sayama |
| 9,060,777 B1 | 6/2015 | Wallace |
| 9,078,658 B2 | 7/2015 | Hewitt |
| 9,107,670 B2 | 8/2015 | Hannes |
| 9,138,213 B2 | 9/2015 | Amin |
| 9,161,758 B2 | 10/2015 | Figulla |
| 9,168,043 B2 | 10/2015 | Van Der Burg |
| 9,179,918 B2 | 11/2015 | Levy |
| 9,186,487 B2 | 11/2015 | Dubrul et al. |
| 9,198,668 B2 | 12/2015 | Theobald |
| 9,198,670 B2 | 12/2015 | Hewitt |
| 9,198,687 B2 | 12/2015 | Fulkerson |
| 9,220,522 B2 | 12/2015 | Fulkerson |
| 9,259,337 B2 | 2/2016 | Cox |
| 9,271,736 B2 | 3/2016 | Heipl |
| 9,295,473 B2 | 3/2016 | Hewitt |
| 9,307,998 B2 | 4/2016 | Chin |
| 9,314,326 B2 | 4/2016 | Wallace |
| 9,387,098 B2 | 7/2016 | Ferrera |
| 9,474,517 B2 | 10/2016 | Amin |
| 9,492,174 B2 | 11/2016 | Hewitt |
| 9,498,604 B2 | 11/2016 | Dubrul |
| 9,532,772 B2 | 1/2017 | Moszner |
| 9,539,122 B2 | 1/2017 | Burke |
| 9,545,300 B2 | 1/2017 | Cully |
| 9,572,698 B2 | 2/2017 | Franano |
| 9,597,087 B2 | 3/2017 | Marchand |
| 9,622,770 B2 | 4/2017 | Trapp |
| 9,629,635 B2 | 4/2017 | Hewitt |
| 9,795,400 B2 | 10/2017 | Davidson |
| 9,826,980 B2 | 11/2017 | Figulla |
| 9,839,430 B2 | 12/2017 | Willems |
| 9,861,467 B2 | 1/2018 | Cully |
| 9,877,726 B2 | 1/2018 | Liu |
| 9,918,720 B2 | 3/2018 | Marchand |
| 9,943,299 B2 | 4/2018 | Khairkhahan |
| 9,955,976 B2 | 5/2018 | Hewitt |
| 9,962,146 B2 | 5/2018 | Hebert |
| 9,980,733 B2 | 5/2018 | Badruddin |
| 10,028,745 B2 | 7/2018 | Morsi |
| 10,028,747 B2 | 7/2018 | Connor |
| 10,076,399 B2 | 9/2018 | Davidson |
| 10,123,803 B2 | 11/2018 | Ferrera et al. |
| 10,136,896 B2 | 11/2018 | Hewitt et al. |
| 10,159,490 B2 | 12/2018 | Wallace et al. |
| 10,231,722 B2 | 3/2019 | Hebert et al. |
| 10,238,393 B2 | 3/2019 | Marchand et al. |
| 10,265,075 B2 | 4/2019 | Porter et al. |
| 10,278,705 B2 | 5/2019 | Amin et al. |
| 10,285,678 B2 | 5/2019 | Hebert et al. |

(56) References Cited

U.S. PATENT DOCUMENTS

| | | |
|---|---|---|
| 10,285,679 B2 | 5/2019 | Hebert et al. |
| 10,285,711 B2 | 5/2019 | Griffin |
| 10,299,775 B2 | 5/2019 | Hebert et al. |
| 10,342,546 B2 | 7/2019 | Sepetka et al. |
| 10,383,635 B2 | 8/2019 | Wallace et al. |
| 10,398,441 B2 | 9/2019 | Warner et al. |
| 10,398,444 B2 | 9/2019 | Morsi |
| 10,433,851 B2 | 10/2019 | Adams et al. |
| 10,478,194 B2 | 11/2019 | Rhee et al. |
| 10,499,939 B2 | 12/2019 | Davidson |
| 10,537,451 B2 | 1/2020 | Franano et al. |
| 10,543,015 B2 | 1/2020 | Walzman |
| 10,543,115 B2 | 1/2020 | Franano et al. |
| 10,548,607 B2 | 2/2020 | Walzman |
| 10,561,411 B1 | 2/2020 | Cole et al. |
| 10,561,441 B2 | 2/2020 | Walzman |
| 10,603,070 B2 | 3/2020 | Walzman |
| 10,610,231 B2 | 4/2020 | Marchand et al. |
| 10,617,428 B2 | 4/2020 | Walzman |
| 10,653,403 B2 | 5/2020 | Hebert et al. |
| 10,716,549 B2 | 7/2020 | Keillor |
| 10,716,573 B2 | 7/2020 | Connor |
| 10,716,574 B2 | 7/2020 | Lorenzo et al. |
| 10,729,447 B2 | 8/2020 | Shimizu et al. |
| 10,743,852 B2 | 8/2020 | Moszner et al. |
| 10,743,884 B2 | 8/2020 | Lorenzo |
| 10,751,065 B2 | 8/2020 | Soto Del Valle et al. |
| 10,751,066 B2 | 8/2020 | Lorenzo |
| 10,772,747 B2 | 9/2020 | Fischer et al. |
| 10,808,341 B2 | 10/2020 | Koppe |
| 10,813,645 B2 | 10/2020 | Hewitt et al. |
| 10,835,257 B2 | 11/2020 | Ferrera et al. |
| 10,856,879 B2 | 12/2020 | Badruddin |
| 10,856,880 B1 | 12/2020 | Badruddin et al. |
| 10,869,672 B2 | 12/2020 | Griffin |
| 10,881,413 B2 | 1/2021 | Merritt et al. |
| 10,888,333 B2 | 1/2021 | Kealey et al. |
| 10,905,430 B2 | 2/2021 | Lorenzo et al. |
| 10,925,612 B2 | 2/2021 | Wallace et al. |
| 10,939,914 B2 | 3/2021 | Hewitt et al. |
| 10,939,915 B2 | 3/2021 | Gorochow et al. |
| 10,952,739 B2 | 3/2021 | Plaza et al. |
| 10,959,735 B2 | 3/2021 | Morsi |
| 10,980,545 B2 | 4/2021 | Bowman et al. |
| 11,006,940 B2 | 5/2021 | Herbert et al. |
| 11,033,277 B2 | 6/2021 | Wolfe et al. |
| 11,045,177 B2 | 6/2021 | Walzman |
| 11,045,203 B2 | 6/2021 | Sepetka et al. |
| 11,058,430 B2 | 7/2021 | Gorochow et al. |
| 11,058,431 B2 | 7/2021 | Pereira et al. |
| 11,076,860 B2 | 8/2021 | Lorenzo |
| 11,076,861 B2 | 8/2021 | Gorochow et al. |
| 11,090,078 B2 | 8/2021 | Walzman |
| 11,090,176 B2 | 8/2021 | Franano et al. |
| 11,123,077 B2 | 9/2021 | Lorenzo et al. |
| 11,134,933 B2 | 10/2021 | Amplatz et al. |
| 11,154,302 B2 | 10/2021 | Lorenzo |
| 11,166,731 B2 | 11/2021 | Wolfe et al. |
| 11,179,159 B2 | 11/2021 | Cox et al. |
| 11,185,335 B2 | 11/2021 | Badruddin et al. |
| 11,202,636 B2 | 12/2021 | Zaidat et al. |
| 11,241,223 B2 | 2/2022 | Herbert et al. |
| 11,253,261 B2 | 2/2022 | Jayaraman |
| 11,266,414 B2 | 3/2022 | Fulton, III |
| 11,284,901 B2 | 3/2022 | Griffin |
| 2001/0041900 A1 | 11/2001 | Callister et al. |
| 2002/0082638 A1 | 6/2002 | Porter et al. |
| 2002/0143349 A1 | 10/2002 | Gifford, II et al. |
| 2002/0169473 A1 | 11/2002 | Sepetka |
| 2002/0188314 A1 | 12/2002 | Anderson et al. |
| 2003/0055451 A1 | 3/2003 | Jones et al. |
| 2003/0120337 A1 | 6/2003 | Tassel et al. |
| 2003/0171739 A1 | 9/2003 | Murphy et al. |
| 2003/0176884 A1 | 9/2003 | Berrada |
| 2003/0181927 A1 | 9/2003 | Wallace |
| 2003/0195553 A1 | 10/2003 | Wallace et al. |
| 2003/0220667 A1 | 11/2003 | Van Der Burg |
| 2004/0034366 A1 | 2/2004 | Burg et al. |
| 2004/0044391 A1 | 3/2004 | Porter |
| 2004/0087998 A1 | 5/2004 | Lee et al. |
| 2004/0093044 A1* | 5/2004 | Rychnovsky .......... A61N 5/062 607/93 |
| 2004/0098027 A1 | 5/2004 | Teoh et al. |
| 2004/0127935 A1 | 7/2004 | Tassel et al. |
| 2004/0133222 A1 | 8/2004 | Tran et al. |
| 2004/0167597 A1 | 8/2004 | Costantino |
| 2004/0172056 A1 | 9/2004 | Guterman |
| 2004/0181253 A1 | 9/2004 | Sepetka |
| 2004/0193246 A1 | 9/2004 | Ferrera |
| 2004/0254594 A1 | 12/2004 | Alfaro |
| 2004/0260332 A1 | 12/2004 | Dubrul |
| 2005/0021016 A1 | 1/2005 | Malecki et al. |
| 2005/0119684 A1 | 6/2005 | Guterman |
| 2005/0251200 A1 | 11/2005 | Porter |
| 2006/0052816 A1 | 3/2006 | Bates et al. |
| 2006/0058735 A1 | 3/2006 | Lesh |
| 2006/0064151 A1 | 3/2006 | Guterman |
| 2006/0116709 A1 | 6/2006 | Sepetka |
| 2006/0116713 A1* | 6/2006 | Sepetka .......... A61B 17/12145 606/200 |
| 2006/0155323 A1 | 7/2006 | Porter et al. |
| 2006/0155367 A1 | 7/2006 | Hines |
| 2006/0167494 A1 | 7/2006 | Suddaby |
| 2006/0206199 A1 | 9/2006 | Churchwell et al. |
| 2007/0043391 A1 | 2/2007 | Moszner et al. |
| 2007/0106311 A1 | 5/2007 | Wallace et al. |
| 2007/0150045 A1 | 6/2007 | Ferrera |
| 2007/0173928 A1 | 7/2007 | Morsi |
| 2007/0198075 A1 | 8/2007 | Levy |
| 2007/0203567 A1 | 8/2007 | Levy |
| 2007/0208376 A1 | 9/2007 | Meng |
| 2007/0225760 A1 | 9/2007 | Moszner |
| 2007/0270902 A1 | 11/2007 | Slazas |
| 2007/0288083 A1 | 12/2007 | Hines |
| 2008/0045995 A1 | 2/2008 | Guterman |
| 2008/0097401 A1 | 4/2008 | Trapp |
| 2008/0097495 A1 | 4/2008 | Feller, III et al. |
| 2008/0147100 A1 | 6/2008 | Wallace |
| 2008/0221600 A1 | 9/2008 | Dieck et al. |
| 2009/0082803 A1 | 3/2009 | Adams |
| 2009/0099647 A1 | 4/2009 | Glimsdale et al. |
| 2009/0192455 A1 | 7/2009 | Ferrera |
| 2009/0209855 A1 | 8/2009 | Drilling et al. |
| 2009/0228029 A1 | 9/2009 | Lee |
| 2009/0281557 A1 | 11/2009 | Sander et al. |
| 2009/0297582 A1 | 12/2009 | Meyer |
| 2009/0318941 A1 | 12/2009 | Sepetka |
| 2010/0069948 A1 | 3/2010 | Veznedaroglu et al. |
| 2010/0174309 A1 | 7/2010 | Fulkerson |
| 2010/0217187 A1 | 8/2010 | Fulkerson |
| 2010/0256600 A1 | 10/2010 | Ferrera |
| 2010/0268204 A1 | 10/2010 | Tieu et al. |
| 2010/0318097 A1 | 12/2010 | Ferrera |
| 2011/0022149 A1 | 1/2011 | Cox |
| 2011/0040319 A1 | 2/2011 | Fulton, III |
| 2011/0046658 A1 | 2/2011 | Connor et al. |
| 2011/0054519 A1 | 3/2011 | Neuss |
| 2011/0082491 A1 | 4/2011 | Sepetka |
| 2011/0152993 A1 | 6/2011 | Marchand et al. |
| 2011/0160763 A1 | 6/2011 | Ferrera et al. |
| 2011/0190797 A1 | 8/2011 | Fulkerson |
| 2011/0202085 A1 | 8/2011 | Loganathan |
| 2011/0264132 A1 | 10/2011 | Strauss |
| 2011/0319926 A1 | 12/2011 | Becking et al. |
| 2011/0319978 A1 | 12/2011 | Schaffer |
| 2012/0016406 A1 | 1/2012 | Ferrera |
| 2012/0041460 A1 | 2/2012 | Ferrera |
| 2012/0041475 A1 | 2/2012 | Ferrera |
| 2012/0071911 A1 | 3/2012 | Sadasivan |
| 2012/0150147 A1 | 6/2012 | Leynov |
| 2012/0165919 A1 | 6/2012 | Cox |
| 2012/0172973 A1 | 7/2012 | Deckard et al. |
| 2012/0271337 A1 | 10/2012 | Figulla et al. |
| 2012/0277788 A1 | 11/2012 | Cattaneo |

(56) References Cited

U.S. PATENT DOCUMENTS

| | | |
|---|---|---|
| 2012/0283768 A1 | 11/2012 | Cox et al. |
| 2012/0330341 A1 | 12/2012 | Becking et al. |
| 2012/0330347 A1 | 12/2012 | Becking |
| 2013/0035628 A1 | 2/2013 | Garrison et al. |
| 2013/0035712 A1 | 2/2013 | Theobald et al. |
| 2013/0066357 A1 | 3/2013 | Aboytes et al. |
| 2013/0066360 A1 | 3/2013 | Becking |
| 2013/0066413 A1 | 3/2013 | Jin |
| 2013/0090682 A1 | 4/2013 | Bachman et al. |
| 2013/0123830 A1 | 5/2013 | Becking |
| 2013/0165967 A1 | 6/2013 | Amin |
| 2013/0190800 A1 | 7/2013 | Murphy |
| 2013/0197622 A1 | 8/2013 | Mitra et al. |
| 2013/0245667 A1 | 9/2013 | Marchand |
| 2013/0274862 A1 | 10/2013 | Cox |
| 2013/0274866 A1 | 10/2013 | Cox |
| 2013/0274868 A1 | 10/2013 | Cox et al. |
| 2014/0005714 A1 | 1/2014 | Quick et al. |
| 2014/0012307 A1 | 1/2014 | Franano et al. |
| 2014/0012363 A1 | 1/2014 | Franano et al. |
| 2014/0018838 A1 | 1/2014 | Franano et al. |
| 2014/0052233 A1 | 2/2014 | Cox |
| 2014/0163609 A1 | 6/2014 | Solem |
| 2014/0172001 A1 | 6/2014 | Becking et al. |
| 2014/0200607 A1 | 7/2014 | Sepetka et al. |
| 2014/0257360 A1 | 9/2014 | Keillor |
| 2014/0257374 A1 | 9/2014 | Heisel et al. |
| 2014/0343602 A1 | 11/2014 | Cox |
| 2014/0358178 A1 | 12/2014 | Hewitt et al. |
| 2015/0105817 A1 | 4/2015 | Marchand |
| 2015/0133990 A1 | 5/2015 | Davidson |
| 2015/0150563 A1 | 6/2015 | Marchand |
| 2015/0250628 A1 | 9/2015 | Monstadt |
| 2015/0272589 A1 | 10/2015 | Lorenzo |
| 2015/0313605 A1 | 11/2015 | Griffin |
| 2015/0351770 A1 | 12/2015 | Fulton, III |
| 2015/0351775 A1 | 12/2015 | Fulton, III |
| 2016/0106437 A1 | 4/2016 | Van Der Burg |
| 2016/0113662 A1 | 4/2016 | Kobayashi et al. |
| 2016/0120551 A1 | 5/2016 | Connor |
| 2016/0174991 A1 | 6/2016 | Chin |
| 2016/0206321 A1 | 7/2016 | Connor |
| 2016/0213380 A1 | 7/2016 | O'Brien |
| 2016/0249934 A1 | 9/2016 | Hewitt et al. |
| 2016/0249935 A1 | 9/2016 | Hewitt et al. |
| 2016/0345979 A1 | 12/2016 | Adams et al. |
| 2017/0128077 A1 | 5/2017 | Hewitt et al. |
| 2017/0156733 A1 | 6/2017 | Becking |
| 2017/0156734 A1 | 6/2017 | Griffin |
| 2017/0172581 A1 | 6/2017 | Bose |
| 2018/0125500 A1 | 5/2018 | Connor |
| 2018/0140305 A1 | 5/2018 | Connor |
| 2018/0193024 A1 | 7/2018 | Walzman |
| 2018/0193043 A1 | 7/2018 | Marchand et al. |
| 2018/0206848 A1 | 7/2018 | Walzman |
| 2018/0206851 A1 | 7/2018 | Walzman |
| 2018/0214158 A1 | 8/2018 | Walzman |
| 2018/0333248 A1 | 11/2018 | Davidson |
| 2019/0008522 A1 | 1/2019 | Lorenzo |
| 2019/0053810 A1 | 2/2019 | Griffin |
| 2019/0059909 A1 | 2/2019 | Griffin |
| 2019/0110796 A1 | 4/2019 | Jayaraman |
| 2019/0183519 A1 | 6/2019 | Imai et al. |
| 2019/0209146 A1 | 7/2019 | Hebert |
| 2019/0209178 A1 | 7/2019 | Richter |
| 2019/0216467 A1 | 7/2019 | Goyal |
| 2019/0223876 A1 | 7/2019 | Badruddin |
| 2019/0223881 A1 | 7/2019 | Hewitt |
| 2019/0231328 A1 | 8/2019 | Hebert |
| 2019/0262002 A1 | 8/2019 | Benjamin |
| 2019/0274691 A1 | 9/2019 | Sepetka |
| 2019/0336132 A1 | 11/2019 | Warner |
| 2019/0343533 A1 | 11/2019 | Costalat |
| 2019/0357914 A1 | 11/2019 | Gorochow |
| 2019/0365472 A1 | 12/2019 | Connor |
| 2019/0374228 A1 | 12/2019 | Wallace |
| 2019/0380718 A1 | 12/2019 | Morsi |
| 2019/0388108 A1 | 12/2019 | Ferrera |
| 2020/0029973 A1 | 1/2020 | Walzman |
| 2020/0038032 A1 | 2/2020 | Rhee |
| 2020/0038035 A1 | 2/2020 | Griffin |
| 2020/0054344 A1 | 2/2020 | Connor |
| 2020/0060702 A1 | 2/2020 | Davidson |
| 2020/0069313 A1 | 3/2020 | Xu |
| 2020/0093499 A1 | 3/2020 | Lorenzo |
| 2020/0100795 A1 | 4/2020 | Connor |
| 2020/0113576 A1 | 4/2020 | Gorochow |
| 2020/0138422 A1 | 5/2020 | Hebert |
| 2020/0155333 A1 | 5/2020 | Franano |
| 2020/0163784 A1 | 5/2020 | Franano |
| 2020/0187952 A1 | 6/2020 | Walsh |
| 2020/0187978 A1 | 6/2020 | Walzman |
| 2020/0253766 A1 | 8/2020 | Walzman |
| 2020/0268365 A1 | 8/2020 | Hebert |
| 2020/0281603 A1 | 9/2020 | Marchand |
| 2020/0289124 A1 | 9/2020 | Rangwala |
| 2020/0289125 A1 | 9/2020 | Dholakia |
| 2020/0289126 A1 | 9/2020 | Hewitt |
| 2020/0305886 A1 | 10/2020 | Soto Del |
| 2020/0323534 A1 | 10/2020 | Shimizu |
| 2020/0337710 A1 | 10/2020 | Lorenzo |
| 2020/0340154 A1 | 10/2020 | Köppe |
| 2020/0345376 A1 | 11/2020 | Fulton, III |
| 2020/0367894 A1 | 11/2020 | Pereira |
| 2020/0367896 A1 | 11/2020 | Zaidat |
| 2020/0367897 A1 | 11/2020 | Wolfe |
| 2020/0367904 A1 | 11/2020 | Becking |
| 2020/0375606 A1 | 12/2020 | Lorenzo |
| 2020/0375607 A1 | 12/2020 | Soto Del Valle |
| 2020/0390455 A1 | 12/2020 | Nguyen et al. |
| 2020/0397447 A1 | 12/2020 | Lorenzo |
| 2020/0405347 A1 | 12/2020 | Walzman |
| 2021/0007755 A1 | 1/2021 | Lorenzo |
| 2021/0022765 A1 | 1/2021 | Walzman |
| 2021/0045750 A1 | 2/2021 | Wolfe |
| 2021/0068842 A1 | 3/2021 | Griffin |
| 2021/0077116 A1 | 3/2021 | Ferrera |
| 2021/0106337 A1 | 4/2021 | Hewitt |
| 2021/0128160 A1 | 5/2021 | Li |
| 2021/0128161 A1 | 5/2021 | Nageswaran |
| 2021/0128162 A1 | 5/2021 | Rhee |
| 2021/0128165 A1 | 5/2021 | Pulugurtha |
| 2021/0128166 A1 | 5/2021 | Kealey |
| 2021/0128167 A1 | 5/2021 | Patel |
| 2021/0128168 A1 | 5/2021 | Nguyen |
| 2021/0128169 A1 | 5/2021 | Li |
| 2021/0129275 A1 | 5/2021 | Nguyen |
| 2021/0137530 A1 | 5/2021 | Greene, Jr. et al. |
| 2021/0145449 A1 | 5/2021 | Gorochow |
| 2021/0153871 A1 | 5/2021 | Griffin |
| 2021/0153872 A1 | 5/2021 | Nguyen et al. |
| 2021/0169496 A1 | 6/2021 | Badruddin et al. |
| 2021/0169499 A1 | 6/2021 | Merritt et al. |
| 2021/0186518 A1 | 6/2021 | Gorochow et al. |
| 2021/0196284 A1 | 7/2021 | Gorochow et al. |
| 2021/0204955 A1 | 7/2021 | Wallace et al. |
| 2021/0219982 A1 | 7/2021 | Badruddin et al. |
| 2021/0251635 A1 | 8/2021 | Soto Del Valle et al. |
| 2021/0259719 A1 | 8/2021 | Griffin |
| 2021/0275184 A1 | 9/2021 | Hewitt et al. |
| 2021/0275188 A1 | 9/2021 | Plaza et al. |
| 2021/0282784 A1 | 9/2021 | Sepetka et al. |
| 2021/0282786 A1 | 9/2021 | Zaidat et al. |
| 2021/0330331 A1 | 10/2021 | Lorenzo |
| 2021/0346032 A1 | 11/2021 | Patterson et al. |
| 2021/0361290 A1 | 11/2021 | Badruddin et al. |
| 2021/0378646 A1 | 12/2021 | Amplatz et al. |
| 2021/0401439 A1 | 12/2021 | Lorenzo et al. |
| 2022/0022884 A1 | 1/2022 | Wolfe et al. |
| 2022/0022886 A1 | 1/2022 | Becking et al. |

(56) References Cited

U.S. PATENT DOCUMENTS

| | | |
|---|---|---|
| 2022/0054141 A1 | 2/2022 | Zaidat et al. |
| 2022/0054286 A1 | 2/2022 | Goyal |

FOREIGN PATENT DOCUMENTS

| | | |
|---|---|---|
| CN | 103099652 | 5/2013 |
| CN | 104168843 | 11/2014 |
| CN | 104958087 | 10/2015 |
| CN | 204931771 | 1/2016 |
| DE | 102008028308 | 4/2009 |
| DE | 102008015781 | 9/2011 |
| DE | 102011102955 | 12/2012 |
| DE | 102009058132 | 7/2014 |
| DE | 202008018523 | 4/2015 |
| DE | 102013106031 | 7/2015 |
| DE | 102012107175 | 8/2015 |
| DE | 102012102844 | 3/2020 |
| DE | 102019121546 | 2/2021 |
| DE | 102019121554 | 2/2021 |
| EP | 0836450 | 4/1988 |
| EP | 0902704 | 3/1999 |
| EP | 1003422 | 5/2000 |
| EP | 1295 563 | 3/2003 |
| EP | 1441649 | 8/2004 |
| EP | 1483009 | 12/2004 |
| EP | 1494619 | 1/2005 |
| EP | 1527753 | 5/2005 |
| EP | 1569565 | 9/2005 |
| EP | 1574169 | 9/2005 |
| EP | 1054635 | 11/2005 |
| EP | 1610666 | 1/2006 |
| EP | 1633275 | 3/2006 |
| EP | 1651117 | 5/2006 |
| EP | 1659988 | 5/2006 |
| EP | 1725185 | 11/2006 |
| EP | 1804719 | 7/2007 |
| EP | 1862122 | 12/2007 |
| EP | 1923005 | 5/2008 |
| EP | 1923019 | 5/2008 |
| EP | 2063791 | 6/2009 |
| EP | 2134263 | 12/2009 |
| EP | 2157937 | 3/2010 |
| EP | 2207500 | 7/2010 |
| EP | 2244666 | 11/2010 |
| EP | 2265193 | 12/2010 |
| EP | 2266465 | 12/2010 |
| EP | 2279023 | 2/2011 |
| EP | 2324775 | 5/2011 |
| EP | 2349024 | 8/2011 |
| EP | 2367482 | 9/2011 |
| EP | 2387951 | 11/2011 |
| EP | 2399524 | 12/2011 |
| EP | 2460476 | 6/2012 |
| EP | 2468349 | 6/2012 |
| EP | 2496299 | 9/2012 |
| EP | 2506808 | 10/2012 |
| EP | 2543345 | 1/2013 |
| EP | 2567663 | 3/2013 |
| EP | 2596754 | 5/2013 |
| EP | 2613709 | 7/2013 |
| EP | 2617386 | 7/2013 |
| EP | 2618709 | 7/2013 |
| EP | 2647343 | 10/2013 |
| EP | 2677944 | 1/2014 |
| EP | 2744412 | 6/2014 |
| EP | 2848211 | 3/2015 |
| EP | 2854704 | 4/2015 |
| EP | 2887887 | 7/2015 |
| EP | 2923674 | 9/2015 |
| EP | 2926744 | 10/2015 |
| EP | 2943152 | 11/2015 |
| EP | 2964105 | 1/2016 |
| EP | 3068337 | 9/2016 |
| EP | 3082619 | 10/2016 |
| EP | 3131515 | 2/2017 |
| EP | 3136986 | 3/2017 |
| EP | 3148481 | 4/2017 |
| EP | 3151904 | 4/2017 |
| EP | 3171793 | 5/2017 |
| EP | 3187117 | 7/2017 |
| EP | 3247285 | 11/2017 |
| EP | 3261703 | 1/2018 |
| EP | 1998686 | 2/2018 |
| EP | 2460477 | 4/2018 |
| EP | 3345553 | 7/2018 |
| EP | 2806825 | 8/2018 |
| EP | 2753246 | 11/2018 |
| EP | 3413808 | 12/2018 |
| EP | 3429479 | 1/2019 |
| EP | 3456271 | 3/2019 |
| EP | 3456272 | 3/2019 |
| EP | 3501429 | 6/2019 |
| EP | 2254505 | 7/2019 |
| EP | 3510945 | 7/2019 |
| EP | 3512459 | 7/2019 |
| EP | 3517055 | 7/2019 |
| EP | 2194885 | 11/2019 |
| EP | 3572010 | 11/2019 |
| EP | 3173037 | 12/2019 |
| EP | 3574851 | 12/2019 |
| EP | 3585275 | 1/2020 |
| EP | 3600068 | 2/2020 |
| EP | 3622901 | 3/2020 |
| EP | 3628242 | 4/2020 |
| EP | 3636173 | 4/2020 |
| EP | 2405820 | 6/2020 |
| EP | 3669800 | 6/2020 |
| EP | 3677192 | 7/2020 |
| EP | 3714812 | 9/2020 |
| EP | 3153114 | 11/2020 |
| EP | 3740138 | 11/2020 |
| EP | 3755276 | 12/2020 |
| EP | 3501428 | 4/2021 |
| EP | 3568088 | 4/2021 |
| EP | 3808284 | 4/2021 |
| EP | 3821825 | 5/2021 |
| EP | 3838186 | 6/2021 |
| EP | 3865079 | 8/2021 |
| EP | 2460478 | 9/2021 |
| EP | 3908208 | 11/2021 |
| EP | 3908209 | 11/2021 |
| EP | 3908354 | 11/2021 |
| FR | 3061647 | 6/2020 |
| IL | 248515 | 7/2019 |
| JP | H02150481 | 6/1990 |
| JP | H0447415 | 4/1992 |
| JP | H08507011 | 7/1996 |
| JP | 2003-175113 | 6/2003 |
| JP | 2005028863 | 2/2005 |
| JP | 2005537092 | 12/2005 |
| JP | 2006509578 | 3/2006 |
| JP | 2010500187 | 1/2010 |
| JP | 2012-501793 | 1/2012 |
| JP | 201203 0497 | 2/2012 |
| JP | 2013-027592 | 2/2013 |
| JP | 2013537069 | 9/2013 |
| RU | 2018131107 | 10/2018 |
| RU | 2019120682 | 9/2019 |
| RU | 2704539 | 10/2019 |
| RU | 2018145502 | 6/2020 |
| RU | 2018145543 | 6/2020 |
| RU | 2019110988 | 10/2020 |
| RU | 2019115837 | 11/2020 |
| RU | 2019116175 | 11/2020 |
| RU | 2019127900 | 3/2021 |
| RU | 2019129351 | 3/2021 |
| RU | 2019129526 | 3/2021 |
| WO | WO 2006/034149 | 3/2006 |
| WO | WO 2006/052322 | 5/2006 |
| WO | WO 2007/076480 | 7/2007 |
| WO | WO 2007/079402 | 7/2007 |
| WO | WO 2008/036156 | 3/2008 |
| WO | WO 2008/151204 | 12/2008 |
| WO | WO 2009/132045 | 10/2009 |

(56) References Cited

FOREIGN PATENT DOCUMENTS

| | | |
|---|---|---|
| WO | WO 2009/135166 | 11/2009 |
| WO | WO 2010/030991 | 3/2010 |
| WO | WO 2010/134914 | 11/2010 |
| WO | WO2011057002 A2 | 5/2011 |
| WO | 2012034135 | 3/2012 |
| WO | WO 2012/032030 | 3/2012 |
| WO | WO 2012/099704 | 7/2012 |
| WO | WO 2012/099909 | 7/2012 |
| WO | WO 2012/099910 | 7/2012 |
| WO | WO 2012/113554 | 8/2012 |
| WO | WO 2012/135037 | 10/2012 |
| WO | WO 2012/163880 | 12/2012 |
| WO | WO 2013/005195 | 1/2013 |
| WO | WO 2013/016618 | 1/2013 |
| WO | WO 2013/028579 | 2/2013 |
| WO | WO 2013/103888 | 7/2013 |
| WO | WO 2013/109309 | 7/2013 |
| WO | WO 2013/152327 | 10/2013 |
| WO | WO 2013/184595 | 12/2013 |
| WO | WO 2014/029835 | 2/2014 |
| WO | WO 2015/095538 | 6/2015 |
| WO | WO 2015/160721 | 10/2015 |
| WO | WO 2015/166013 | 11/2015 |
| WO | WO 2015/184075 | 12/2015 |
| WO | WO 2015/187196 | 12/2015 |
| WO | WO 2016/107357 | 7/2016 |
| WO | WO 2016/118420 | 7/2016 |
| WO | WO 2016/137997 | 9/2016 |
| WO | WO 2017/106567 | 6/2017 |
| WO | WO 2017/139702 | 8/2017 |
| WO | WO 2017/156275 | 9/2017 |
| WO | WO 2017/161283 | 9/2017 |
| WO | WO 2018/051187 | 3/2018 |
| WO | WO 2018/130624 | 7/2018 |
| WO | WO 2018/156833 | 8/2018 |
| WO | WO 2018/175221 | 9/2018 |
| WO | WO 2019/143755 | 7/2019 |
| WO | WO 2019/165360 | 8/2019 |
| WO | WO 2020/139544 | 7/2020 |
| WO | WO 2020/150023 | 7/2020 |
| WO | WO 2020/190620 | 9/2020 |
| WO | WO 2020/190630 | 9/2020 |
| WO | WO 2020/190639 | 9/2020 |
| WO | WO 2020/243039 | 12/2020 |
| WO | WO 2021/028160 | 2/2021 |
| WO | WO 2021/028161 | 2/2021 |
| WO | WO 2021/051110 | 3/2021 |
| WO | WO 2021/087610 | 5/2021 |
| WO | WO 2021/092620 | 5/2021 |
| WO | WO 2021/183793 | 9/2021 |

OTHER PUBLICATIONS

Altes et al., "Creation of Saccular Aneurysms in the Rabbit: A Model Suitable for Testing Endovascular Devices," AJR Am J Roentgenol, 2000, 174(2):349-354.
Blackshear et al., "Appendage obliteration to reduce stroke in cardiac surgical patients with atrial fibrillation," Ann. Thorac. Surg., Feb. 1996, 61(2):755-9.
Gottlieb et al., "Anticoagulation in atrial fibrillation. Does efficacy in clinical trials translate into effectiveness in practice?" Arch. Intern. Med., Sep. 1994, 154(17):1945-53.
International Preliminary Report on Patentability in International Application No. PCT/EP2015/059429, dated Jul. 13, 2016, 11 pages.
International Search Report and Written Opinion in International Appln. No. PCT/EP2018/072576, dated Nov. 21, 2018, 20 pages.
International Search Report and Written Opinion in International Appln. PCT/EP2015/059429, dated Jul. 6, 2015, 5 pages.
ISA/EP, International Search Report for PCT/EP2017/055765 (dated Apr. 18, 2017).
JP Office Action in Japanese Appln. 2017-508761, dated Nov. 27, 2018, 4 pages (English translation).
JP Office Action in Japanese Appln. No. 2017-508761, dated Mar. 19, 2019, 3 pages (English translation).
Schaffer, "Biocompatible Wire," Advanced Materials & Processes, Oct. 2002, pp. 51-54.
Bosworth et al., "Gamma irradiation of electrospun poly(e-caprolactone) fibers affects material properties but not cell response," Journal of Polymer Science PartB: Polymer Physics, Apr. 2012, pp. 870-876.
CA Office Action in Canadian Appln. No. 2,946,078, dated May 26, 2021, 4 pages.
CN Office Action in Chinese Appln. No. 201580035663.X, dated Aug. 1, 2018, 27 pages (with English Translation).
CN Office Action in Chinese Appln. No. 201780024233.7, dated Apr. 22, 2021, 6 pages (with English translation).
CN Office Action in Chinese Appln. No. 201780024233.7, dated Jul. 9, 2020, 20 pages (with English Translation).
CN Office Action in Chinese Appln. No. 201780024233.7, dated Oct. 22, 2020, 17 pages (with English Translation).
EP Extended Search Report in European Appln, No. 19159876,2, dated Jun. 14, 2019, 9 pages.
EP Extended Search Report in European Appln, No. 20201759,6, dated Nov. 12, 2020, 12 pages.
EP Office Action in European Appln No. 16808631,2, dated Aug. 16, 2019, 8 pages.
Izadi et al., "Teflon hierarchical nanopillars with dry and wet adhesive properties," Journal of Polymer Science Part B: Polymer Physics, Apr. 2012, pp. 846-851.
JP Office Action in Japanese Appln. No. 2018-548075, dated Mar. 25, 2021, 8 pages (with English translation).
Ohta et al., "Size control of phase-separated liquid crystal droplets in a polymer matrix based on the phase diagram," Journal of Polymer Science Part B: Polymer Physics, Apr. 2012, pp. 863-869.
Popov et al., "Interacting nanoparticles with functional surface groups," Journal of Polymer Science Part B: Polymer Physics, Mar. 2012, pp. 852-862.
U.S. Appl. No. 14/699,188, filed Nov. 5, 2015.
U.S. Appl. No. 15/372,128, filed May 14, 2019.
U.S. Appl. No. 16/080,626, filed Aug. 28, 2018.
U.S. Appl. No. 16/172,157, filed Oct. 26, 2018.
U.S. Appl. No. 16/590,821, filed Oct. 2, 2019.
U.S. Appl. No. 16/640,142, filed Feb. 19, 2020.
U.S. Appl. No. 16/796,788, filed Feb. 20, 2020.
U.S. Appl. No. 16/952,756, filed Nov. 19, 2020.
JP Office Action in Japanese Application No. 2018-529554, dated Jul. 12, 2021, 6 pages (with English translation).
JP Office Action in Japanese Application No. 2018-529554, dated Sep. 15, 2020, 6 pages (with English translation).
JP Office Action in Japanese Application No. 2019-145966, dated Sep. 1, 2020, 6pages (with English translation).
PCT International Preliminary Report on Patentability in International Application No. PCT/EP2016/080152, dated Jun. 12, 2018, 10 pages.
PCT International Preliminary Report on Patentability in International Application No. PCT/EP2017/055765, dated Sep. 11, 2018, 9 pages.
PCT International Written Opinion in International Application No. PCT/EP2021/054103, dated Aug. 26, 2021, 4 pages.
JP Office Action in Japanese Appln. No. 2018-529554, dated Nov. 30, 2020, 11 pages (with English translation).
International Search Report and Written Opinion; PCT/EP2016/080152; dated Jun. 16, 2017; 21 pages.
PCT Form ISA/206—Invitation To Pay Additional Fees, which issued on Feb. 24, 2017 in corresponding PCT application PCT/EP2016/080152.
PCT International Preliminary Report on Patentability in International Appln. No. PCT/EP2019/072576, dated Feb. 25, 2020, 12 pages.

* cited by examiner

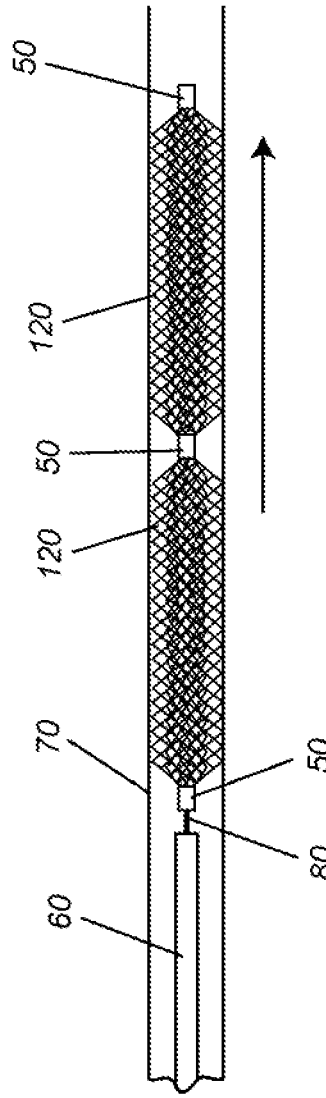
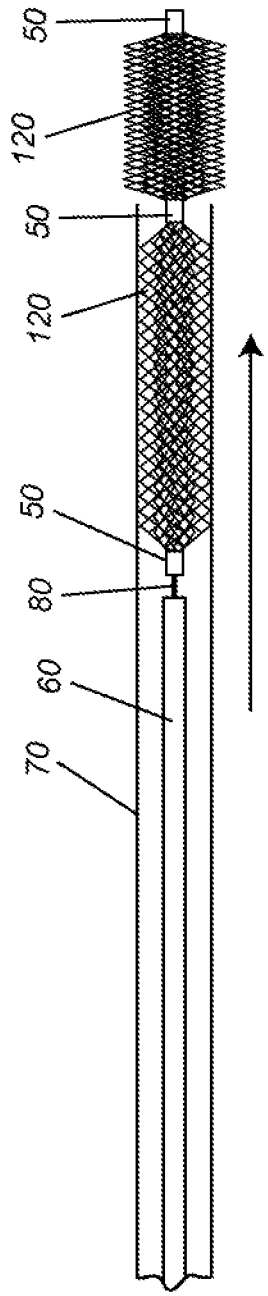

OCCLUSION DEVICE

RELATED APPLICATIONS

This application is a continuation of U.S. application Ser. No. 15/372,128 filed on Dec. 7, 2016 and claims the benefit of U.S. Provisional Application No. 62/264,171 filed on Dec. 7, 2015. All documents and references cited herein, and in the above referenced applications, are hereby incorporated by reference.

FIELD OF THE INVENTION

The occlusion device disclosed herein relates generally to the field of occlusion devices and/or occlusion device systems and/or implantable occlusion devices and the use of the same for the occlusion of vessels and/or the treatment and/or amelioration of aneurysms and/or for peripheral vascular embolization (a process well known in the art and known to involve the shutdown of blood flow distal to a specified vascular point), for example, in the treatment and/or amelioration of peripheral arterial or venous pathologies and/or any related pathologies requiring vessel occlusion for the treatment thereof.

BACKGROUND OF THE DISCLOSURE

There is a significant demand for the development of improved occlusion devices and/or systems for the treatment and/or amelioration of aneurysms. This observation is supported by the abundance and wide-range of current occlusion devices and/or systems currently in the aneurysm peripheral vascular embolization treatment field. However, there still remains an unmet need for providing aneurysm treatment and/or amelioration, particularly for neurovascular aneurysms, via occlusion devices comprised of a deployable material designed to achieve greater flow disruption and compartmentalization to introduce stasis and/or designed in such a manner so as to occlude larger and/or more irregularly shaped aneurysms.

It is well known that an aneurysm forms when a dilated portion of an artery is stretched thin from the pressure of the blood. The weakened part of the artery forms a bulge, or a ballooning area, that risks leak and/or rupture. When a neurovascular aneurysm ruptures, it causes bleeding into the compartment surrounding the brain, the subarachnoid space, causing a subarachnoid hemorrhage. Subarachnoid hemorrhage from a ruptured neurovascular aneurysm can lead to a hemorrhagic stroke, brain damage, and death. Approximately 25 percent of all patients with a neurovascular aneurysm suffer a subarachnoid hemorrhage. Neurovascular aneurysms occur in two to five percent of the population and more commonly in women than men. It is estimated that as many as 18 million people currently living in the United States will develop a neurovascular aneurysm during their lifetime. Annually, the incidence of subarachnoid hemorrhage in the United States exceeds 30,000 people. Ten to fifteen percent of these patients die before reaching the hospital and over 50 percent die within the first thirty days after rupture. Of those who survive, about half suffer some permanent neurological deficit.

Smoking, hypertension, traumatic head injury, alcohol abuse, use of hormonal contraception, family history of brain aneurysms, and other inherited disorders such as Ehlers-Danlos syndrome (EDS), polycystic kidney disease, and Marfan syndrome possibly contribute to neurovascular aneurysms.

Most unruptured aneurysms are asymptomatic. Some people with unruptured aneurysms experience some or all of the following symptoms: peripheral vision deficits, thinking or processing problems, speech complications, perceptual problems, sudden changes in behavior, loss of balance and coordination, decreased concentration, short term memory difficulty, and fatigue. Symptoms of a ruptured neurovascular aneurysm include nausea and vomiting, stiff neck or neck pain, blurred or double vision, pain above and behind the eye, dilated pupils, sensitivity to light, and loss of sensation. Sometimes patients describing "the worst headache of my life" are experiencing one of the symptoms of a ruptured neurovascular aneurysm.

Most aneurysms remain undetected until a rupture occurs. Aneurysms, however, may be discovered during routine medical exams or diagnostic procedures for other health problems. Diagnosis of a ruptured cerebral aneurysm is commonly made by finding signs of subarachnoid hemorrhage on a CT scan (Computerized Tomography). If the CT scan is negative but a ruptured aneurysm is still suspected, a lumbar puncture is performed to detect blood in the cerebrospinal fluid (CSF) that surrounds the brain and spinal cord.

To determine the exact location, size, and shape of an aneurysm, neuroradiologists use either cerebral angiography or tomographic angiography. Cerebral angiography, the traditional method, involves introducing a catheter into an artery (usually in the leg) and steering it through the blood vessels of the body to the artery involved by the aneurysm. A special dye, called a contrast agent, is injected into the patient's artery and its distribution is shown on X-ray projections. This method may not detect some aneurysms due to overlapping structures or spasm.

Computed Tomographic Angiography (CTA) is an alternative to the traditional method and can be performed without the need for arterial catheterization. This test combines a regular CT scan with a contrast dye injected into a vein. Once the dye is injected into a vein, it travels to the brain arteries, and images are created using a CT scan. These images show exactly how blood flows into the brain arteries. New diagnostic modalities promise to supplement both classical and conventional diagnostic studies with less-invasive imaging and possibly provide more accurate 3-dimensional anatomic information relative to aneurismal pathology. Better imaging, combined with the development of improved minimally invasive treatments, will enable physicians to increasingly detect, and treat, more silent aneurysms before problems arise.

Several methods of treating aneurysms have been attempted, with varying degrees of success. For example, open craniotomy is a procedure by which an aneurysm is located, and treated, extravascularly. This type of procedure has significant disadvantages. For example, the patient undergoes a great deal of trauma in the area of the aneurysm by virtue of the fact that the surgeon must sever various tissues in order to reach the aneurysm. In treating cerebral aneurysms extravascularly, for instance, the surgeon must typically remove a portion of the patient's skull, and must also traumatize brain tissue in order to reach the aneurysm. As such, there is a potential for the development of epilepsy in the patients due to the surgery.

Other techniques used in treating aneurysms are performed endovascularly. Such techniques typically involve attempting to form a mass within the sac of the aneurysm. Typically, a microcatheter is used to access the aneurysm. The distal tip of the microcatheter is placed within the sac of the aneurysm, and the microcatheter is used to inject embolic material into the sac of the aneurysm. The embolic material includes, for example, detachable coils or an embolic agent, such as a liquid polymer. The injection of these types of embolic materials suffers from disadvantages, most of which are associated with migration of the embolic material out of the aneurysm into the parent artery. This can cause permanent and irreversible occlusion of the parent artery.

For example, when detachable coils are used to occlude an aneurysm which does not have a well-defined neck region, the detachable coils can migrate out of the sac of the aneurysm and into the parent artery. Further, it is at times difficult to gauge exactly how full the sac of the aneurysm is when detachable coils are deployed. Therefore, there is a risk of overfilling the aneurysm in which case the detachable coils also spill out into the parent artery.

Another disadvantage of detachable coils involves coil compaction over time. After filling the aneurysm, there remains space between the coils. Continued hemodynamic forces from the circulation act to compact the coil mass resulting in a cavity in the aneurysm neck. Thus, the aneurysm can recanalize.

Embolic agent migration is also a problem. For instance, where a liquid polymer is injected into the sac of the aneurysm, it can migrate out of the sac of the aneurysm due to the hemodynamics of the system. This can also lead to irreversible occlusion of the parent vessel.

Techniques have been attempted in order to deal with the disadvantages associated with embolic material migration to the parent vessel. Such techniques are, without limitation, temporary flow arrest and parent vessel occlusion, and typically involve temporarily occluding the parent vessel proximal of the aneurysm, so that no blood flow occurs through the parent vessel, until a thrombotic mass has formed in the sac of the aneurysm. In theory, this helps reduce the tendency of the embolic material to migrate out of the aneurysm sac. However, it has been found that a thrombotic mass can dissolve through normal lysis of blood. Also, in certain cases, it is highly undesirable from a patient's risk/benefit perspective to occlude the parent vessel, even temporarily. Therefore, this technique is, at times, not available as a treatment option. In addition, it is now known that even occluding the parent vessel may not prevent all embolic material migration into the parent vessel.

Another endovascular technique for treating aneurysms involves inserting a detachable balloon into the sac of the aneurysm using a microcatheter. The detachable balloon is then inflated using saline and/or contrast fluid. The balloon is then detached from the microcatheter and left within the sac of the aneurysm in an attempt to fill the sac of the aneurysm. However, detachable balloons also suffer disadvantages and as such this practice has all but been superseded by the current practice of deployment of coils or other types of occlusion devices. For example, detachable balloons, when inflated, typically will not conform to the interior configuration of the aneurysm sac. Instead, the detachable balloon requires the aneurysm sac to conform to the exterior surface of the detachable balloon. Thus, there is an increased risk that the detachable balloon will rupture the sac of the aneurysm. Further, detachable balloons can rupture and migrate out of the aneurysm.

Another endovascular technique for treating aneurysms involves occlusion devices having two expandable lobes and a waist, or an expandable body portion, a neck portion, and a base portion.

Still another endovascular technique for treating aneurysms involves occlusion devices for intrasaccular implantation having a body portion designed to fill and/or expand radially into the space within the sac of the aneurysm.

Still another endovascular technique is disclosed in the co-owned pending application, U.S. Ser. No. 14/699,188, incorporated herein in its entirety by reference.

Many current occlusion devices are not designed for treatment of large aneurysms or for aneurysms of irregular shapes and sizes, including wide- and narrow-necked aneurysms, side-wall and bifurcation aneurysms, for example. Many current occlusion devices are constructed of braided or woven mesh designs and such designs, if reconfigured for a large and irregular shaped aneurysm, would typically utilize too much material. This would make it difficult to collapse down into a constrained, low profile, delivery configuration small enough to be delivered and deployed without excess friction on the walls of the deliver catheter or other delivery lumen. The sheer bulkiness of these devices would make them inconvenient or inappropriate for intracranial delivery.

Therefore, the occlusion device disclosed herein provides innovative improvements and several advantages in the field of vascular occlusion devices because the occlusion device disclosed herein provides aneurysm and/or body lumen treatment and/or amelioration, particularly for neurovascular aneurysms of large and irregular sizes, via the use of super compactable continuous mesh-based fully-retrievable deployable material. The occlusion devices disclosed herein are comprised of a mesh-based deployable continuous structure having compressible axial mesh carriages configured end to end and defined on either end by pinch points in the continuous mesh structure. This novel design achieves greater flow disruption and compartmentalization within the aneurysm or body lumen and results in increased stasis particularly so as to occlude larger and more irregularly shaped aneurysms.

All documents and references cited herein and in the referenced patent documents, are hereby incorporated herein by reference.

SUMMARY OF THE INVENTION

The present inventor has designed an intra-aneurysmal occlusion device for deploying into the aneurysm sac providing aneurysm treatment and/or amelioration through the creation of flow disruption and ultimate stasis. The occlusion device uniquely comprises a series of compressible mesh carriages which have discreet pinch points defining the carriages at each end and providing a continuous 3-dimensional mesh network inside the aneurysm for flow disruption, thrombus establishment, and/or a framework for cell growth. Such an implantable occlusion device is also used for treatment of vessel occlusion and/or peripheral vascular embolization.

Disclosed herein is an occlusion device for implantation into a body lumen or aneurysm, the occlusion device comprising a continuous compressible mesh structure comprising axial mesh carriages configured end to end, wherein each end of each carriage is a pinch point in the continuous mesh structure.

In one embodiment, a marker encircles at least one pinch point of the continuous mesh structure. In a further embodiment, the marker is radiopaque.

In another embodiment, at least one mesh carriage of the continuous mesh structure comprises an inner coaxial mesh carriage or inner coaxial mesh carriages. In a further embodiment, the inner coaxial mesh carriage or carriages is dissimilar material to its outer mesh carriage. In a further embodiment, the inner coaxial mesh carriages are two (2) or three (3) inner coaxial mesh carriages. In another further embodiment, the inner coaxial mesh carriage or carriages is dissimilar mesh density to its outer mesh carriage.

In another embodiment, the continuous mesh structure expands to a deployed shape and fills the body lumen or aneurysm.

In another embodiment, the number (n) of axial mesh carriages is two (2), three (3), four (4) or five (5) axial mesh carriages.

Also disclosed herein is a kit for treatment and/or amelioration of a body lumen or an aneurysm; the kit comprising an occlusion device for implantation into a body lumen or aneurysm comprising, a continuous compressible mesh structure comprising axial mesh carriages configured end to end, wherein each end of each carriage is a pinch point in the continuous mesh structure; and a delivery system or detachment system corresponding to the occlusion device. In one embodiment, the delivery system of the kit is a microcatheter, catheter, guide wire, or pusher wire. In another embodiment, the detachment system of the kit is an electrolytic detachment system.

Also disclosed herein is a method for treating or ameliorating a body lumen or an aneurysm in a patient, the method comprising delivering to a body lumen or an aneurysm an occlusion device comprising, a continuous compressible mesh structure comprising axial mesh carriages configured end to end, wherein each end of each carriage is a pinch point in the continuous mesh structure; and deploying the occlusion device in the aneurysm, thereby treating or ameliorating the aneurysm in the patient.

In another embodiment, disclosed herein is an occlusion device for implantation into a body lumen or aneurysm comprising, a compressible continuous mesh structure comprising an axial mesh carriage, wherein each end of the carriage is a pinch point in the continuous mesh structure, and wherein the carriage comprises inner coaxial mesh carriages.

Additionally, disclosed herein are methods for manufacture and/or delivery and/or deployment of the occlusion device disclosed herein.

In other embodiments, the occlusion device in the preceding paragraphs may incorporate any of the preceding or subsequently disclosed embodiments.

The Summary of the Invention is not intended to define the claims nor is it intended to limit the scope of the invention in any manner.

Other features and advantages of the invention will be apparent from the following Drawings, Detailed Description, and the Claims.

BRIEF DESCRIPTION OF THE FIGURES

FIG. 1A shows a mesh carriage embodiment of the occlusion device disclosed herein. FIG. 1B shows a series of mesh carriages of the occlusion device disclosed herein.

FIG. 7 illustrates a perspective view of an embodiment of the electrolytic delivery and/or deployment and/or detachment of an occlusion device disclosed herein and shows the delivery via a catheter lumen and/or pusher wire having electrolytic means of an occlusion device disclosed herein having mesh carriages and inner mesh carriages.

FIG. 8 illustrates a perspective view of an embodiment of the electrolytic delivery and/or deployment and/or detachment of an occlusion device disclosed herein and shows device deployment and electrolytic detachment of a pusher wire from the occlusion device disclosed herein having a series of mesh carriages and inner coaxial mesh carriages.

DETAILED DESCRIPTION

Figure 1A:
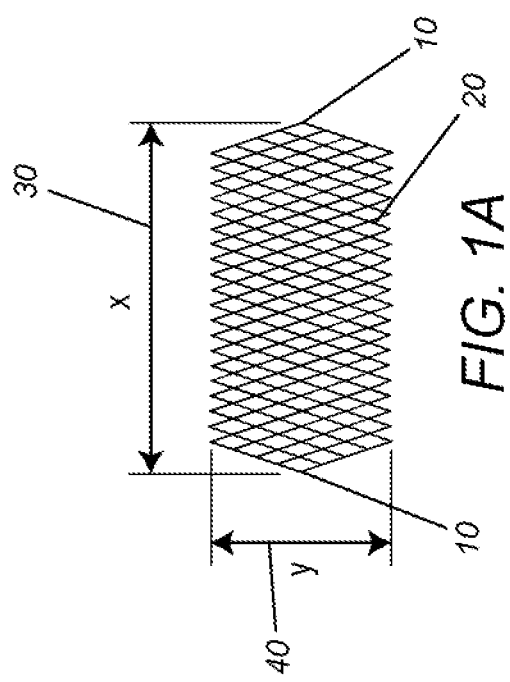
FIG. 1A-1B illustrates perspective views of an embodiment of an occlusion device disclosed herein.

The occlusion device disclosed herein is illustrated in the drawings and description in which like elements are assigned the same reference numerals. However, while particular embodiments are illustrated in the drawings, there is no intention to limit the occlusion device disclosed herein to the specific embodiment or embodiments disclosed. Rather, the occlusion device disclosed herein is intended to cover all modifications, alternative constructions, and equivalents falling within the spirit and scope of the invention. As such, the drawings are intended to be illustrative and not restrictive.

Unless otherwise defined, all technical terms used herein have the same meaning as commonly understood by one of ordinary skill in the art to which this technology belongs.

Exemplary embodiments of the occlusion device disclosed herein are depicted in FIGS. 1-10.

For the purposes of the occlusion device disclosed herein, the terminology "corresponds to" means there is a functional and/or mechanical relationship between objects which correspond to each other. For example, an occlusion device delivery system corresponds to (or is compatible with) an occlusion device for deployment thereof.

For the purposes of the occlusion device disclosed herein, the terminology "occlusion device" means and/or may be interchangeable with terminology such as, without limitation, "device" or "occlusion device system" or "occlusion system" or "system" or "occlusion device implant" or "implant" or "intrasaccular implant" or "intra-aneurysmal implant" and the like.

Occlusion device delivery systems are well known and readily available in the art. For example, such delivery technologies may be found, without limitation, in U.S. Pat. Nos. 4,991,602; 5,067,489; 6,833,003; and Publication Numbers 2006/0167494; and 2007/0288083; each of the teachings of which are incorporated herein. For the purposes of the occlusion device disclosed herein, any type of occlusion device delivery means and/or delivery system and/or delivery technology and/or delivery mechanism and/or detachment (and/or attachment) means and/or detachment system and/or detachment technology and/or detachment mechanism may be utilized and/or modified in such a manner as to make compatible (so as to correspond) with the occlusion device disclosed herein. Exemplary occlusion device delivery mechanisms and/or systems include, without limitation, guide wires, pusher wires, catheters, micro-catheters, and the like. Exemplary occlusion device detachment mechanisms include, without limitation, fluid pressure, electrolytic mechanisms, hydraulic mechanisms, interlocking mechanisms, and the like. In one embodiment, the occlusion device disclosed herein is used in a method of electrolytic detachment. Electrolytic detachment is well known in the art and can be found, for example, in U.S. Pat. Nos. 5,122,136; 5,423,829; 5,624,449; 5,891,128; 6,123,714; 6,589,230; and 6,620,152.

The occlusion device disclosed herein comprises a series of compressible mesh 20 carriages having discreet 10 pinch points at each end of each 20 carriage. In this respect, the occlusion device design is one continuous 3-dimensional mesh network which, when deployed in an 90 aneurysm or body lumen, provides flow disruption, thrombus establishment, a framework for cell growth, and/or ultimate stasis. For the purposes of the claimed invention, a 20 "carriage" is an axial segment of mesh between each 10 pinch point or each 50 marker-encircled 10 pinch point. A 10 "pinch point" is located at and defines the ends of an axial segment of mesh. Such segmented mesh 20 carriages and 10 pinch points are, in many instances, within a continuous mesh structure or network. A "pinch point" is as a constrained and gathered location on the mesh structure which functions to restrict movement of the adjacent carriages at an isolated point and thereby stabilizes the carriages relative to each other. The number (n) of these 20 carriages is as many as clinically and practically possible, and determined by a clinician in accordance with known diagnostic techniques in advance, for treating large and/or irregular-sized 90 aneurysms, and for delivery through about a 150 centimeter (cm) 70 catheter (or micro-catheter). The 30 length (x) of each 20 carriage can vary depending on the number (n) of 20 carriages deemed appropriate to occlude an 90 aneurysm of a given size so long as the 30 length (x) is sufficient to permit the 20 carriage to expand to dimension y (40 width) in "free air." As is accepted in the art, the diameter of such an occlusion device is measured in free air. The 40 width (y) of each 20 carriage ranges (in free air) from about 2 millimeters (mm) to about 50 mm in order to be clinically practical. When deployed, the 20 carriage compresses in such a manner where the diameter or 40 width (y) grows or expands up to about a factor of two (2) such that a 20 carriage of 40 y dimension is capable of growing to approximately 2 times 40 y (or 2y). In other words, each 20 carriage compresses like a marshmallow which causes 30 x to be reduced and 40 y to expand. In one embodiment, in free air, each 20 carriage can be designed in such a manner that 30 x is greater or equal to 40 y but in the deployed (compressed) shape, 40 y is greater than 30 x. Such an occlusion device comprising a series of compressible 20 carriages can be constructed in a variable manner so as to select the number (n) of the 20 carriages as well as the 30 length (x) and 40 width (y) of each 20 carriage to accommodate a wide range of sizes and shapes of 90 aneurysms or body lumen to be treated. As such, in another embodiment, in free air, each 20 carriage can be designed in such a manner that 30 x is equal to or less than 40 y and in the deployed (compressed) shape, 40 y remains greater than 30 x.

In one embodiment, the device is constructed of a metal braid of readily available material such as, without limitation, nitinol (NiTi), cobalt chrome (CoCr) alloy, stainless steel, tungsten iridium alloy or a combination thereof. For example, the mesh 20 carriages are woven with the most clinically relevant and practical braided mesh in a range of as few as 36 braids to as many as 144 braids. In another embodiment, the angle of the weave of the metal braid construction creates the softest compressible mesh design. For example, the mesh is braided with a wire diameter of about 0.0075 inches up to about 0.005 inches. Accordingly, the occlusion device disclosed herein is a series of ultra-soft axially compressible mesh 20 carriages, wherein n=to the number of mesh 20 carriages in a single occlusion device. Prior to use of such an occlusion device having "n" carriages, a clinician or physician determines the size and shape of the aneurysm or body lumen to be treated using readily available diagnostic techniques. The physician or clinician is then able to best choose the occlusion device having the desired number (n) of carriages, and various sizes thereof, which will be used to best treat the given aneurysm or body lumen.

Figure 1B:
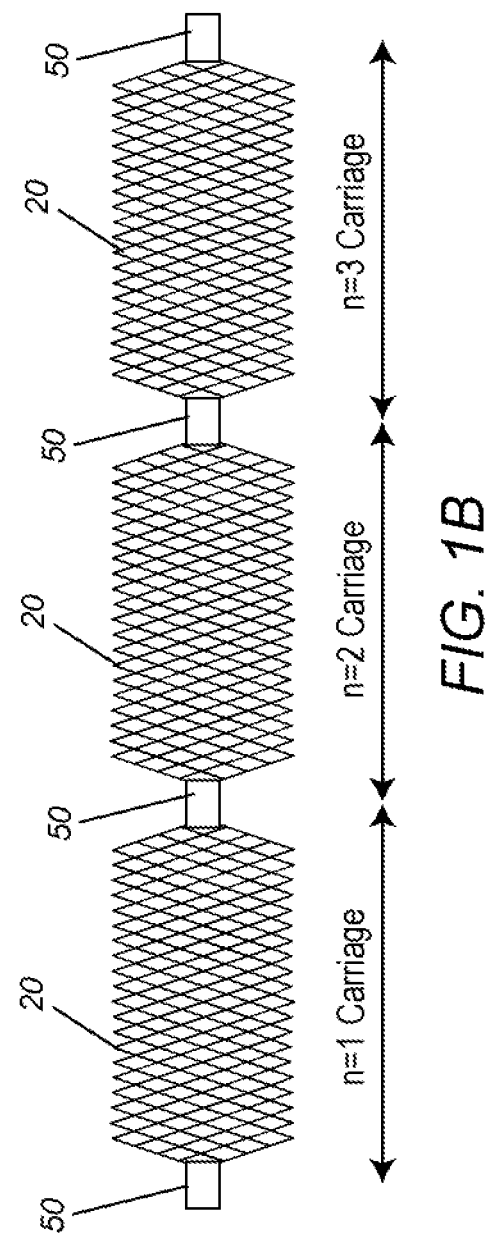
Figure 2:
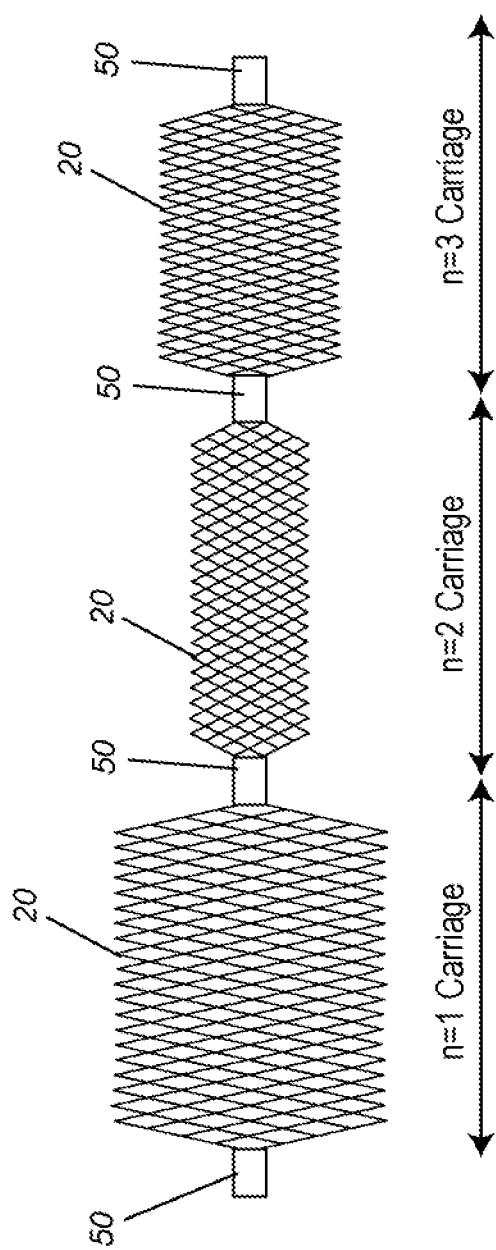
FIG. 2 illustrates a perspective view of an embodiment of a series of variable mesh carriages of the occlusion device disclosed herein.

FIG. 1A shows an exemplary embodiment of a singular mesh 20 carriage having an axial 30 length (x) which is greater than its 40 width (y) in free air, and wherein each end of the 20 carriage is a 10 pinch point. In another embodiment, the axial 20 carriage can have an axial 30 length (x) which is equal to its 40 width (y) in free air. In yet another embodiment, the axial 20 carriage can have an axial 30 length (x) which is less than its 40 width (y) in free air. FIG. 1B shows an embodiment of a series of axial mesh segmented 20 carriages in a continuous compressible mesh structure, wherein n=three (3) axial mesh 20 carriages, and wherein each 10 pinch point is encircled by a 50 marker. "Markers" are well known and readily available in the medical device art. In some embodiments, a marker consists of metallic material, often radiopaque material, and takes the form of a shape such as a band-shaped marker, a ring-shaped marker, a tube-shaped, and the like, so as to encircle a pinch point of the occlusion device. Alternatively, a marker may consist of wire strands wound around and therefore encircling a given pinch point. In one embodiment, the 50 markers which encircle each 10 pinch point provide positional reference under X-Ray as to where the device is located in the 70 catheter (or microcatheter) and where the device is located once deployed in an 90 aneurysm or body lumen. FIG. 2 shows an exemplary embodiment of a series of variably-sized (differing in size and/or diameter) segmented axial mesh 20 carriages in a continuous compressible mesh structure, wherein n=three (3) axial mesh 20 carriages, wherein each 20 carriage varies with respect to the dimensions of 30 x and 40 y, and wherein each 10 pinch point is encircled by a 50 marker. In such a configuration as shown in FIG. 2, the first 20 carriage (on the right) to enter the 90 aneurysm will have a diameter or 40 width (y) which is slightly larger than the largest measured diameter of an 90 aneurysm to be treated which ensures the continuous mesh structure of the device will not come in contact with the dome of the 90 aneurysm which often is the thinnest and most sensitive area of the 90 aneurysm's wall. Additionally, in this configuration as shown in FIG. 2, the diameter or 40 width (y) of the last 20 carriage (on the left) to enter the 90 aneurysm will be larger than the 100 aneurysm neck which ensures this last 20 carriage remains secure (and is anchored) inside the 90 aneurysm.

Figure 3:
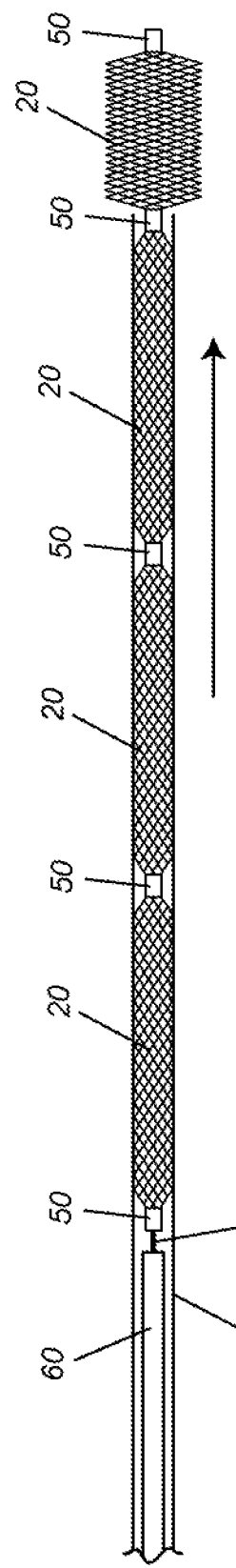
FIG. 3 illustrates perspective views of an embodiment of the delivery and/or deployment of an occlusion device disclosed herein having a series of mesh carriages.

FIG. 3 shows an embodiment of the occlusion device as disclosed herein with the constrained mesh 20 carriages of the device loaded within a 70 catheter lumen. The device is advanced with an electrolytic 60 pusher wire having an 80 electrolytic detachment zone and when deployed, the 20 carriage expands as it exits the 70 catheter tip to occupy the volume of the 90 aneurysm or body lumen. As the subsequent axial 20 carriages are deployed into the 90 aneurysm, they compress against each other filling the 90 aneurysm thereby creating a series of layers and/or compartments inside the 90 aneurysm or body lumen which disrupts flow and ultimately creates stasis.

Figure 4:
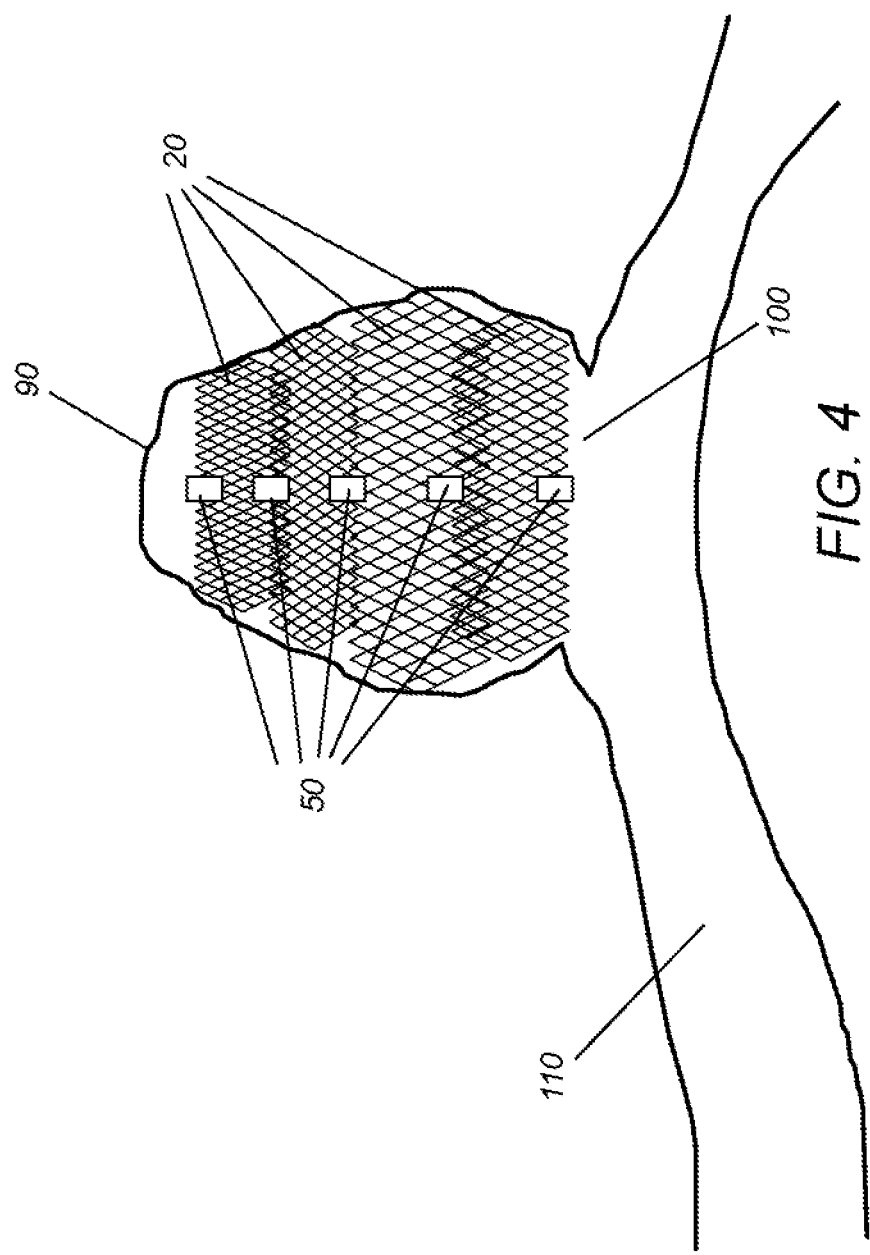
FIG. 4 illustrates perspective views of an embodiment of an occlusion device disclosed herein having a series of mesh carriages deployed in an aneurysm.

FIG. 4 shows an embodiment of an occlusion device as disclosed herein deployed within an 90 aneurysm to be treated. The compressible mesh 20 carriages create multiple layers of compartmentalization inside the 90 aneurysm sac. In this deployed shape, the axial 20 carriages fill the 90 aneurysm or body lumen as layers or compartments thereby transforming the deployed axial 30 length (x) to a proportion of its axial 30 length in free air. For example, deployed axial 30 length (x) is about 5% to about 50% of the axial 30 length in free air.

Figure 10:
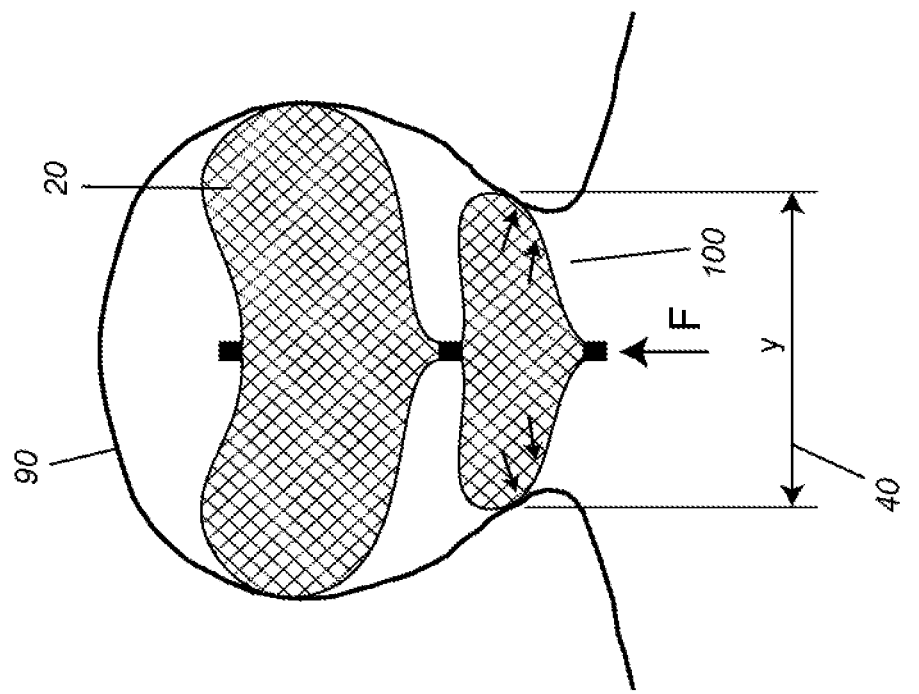
FIG. 10 illustrates a perspective view of an embodiment of an occlusion device disclosed herein having a series of two variably sized mesh carriages deployed in an aneurysm.
Figure 9:
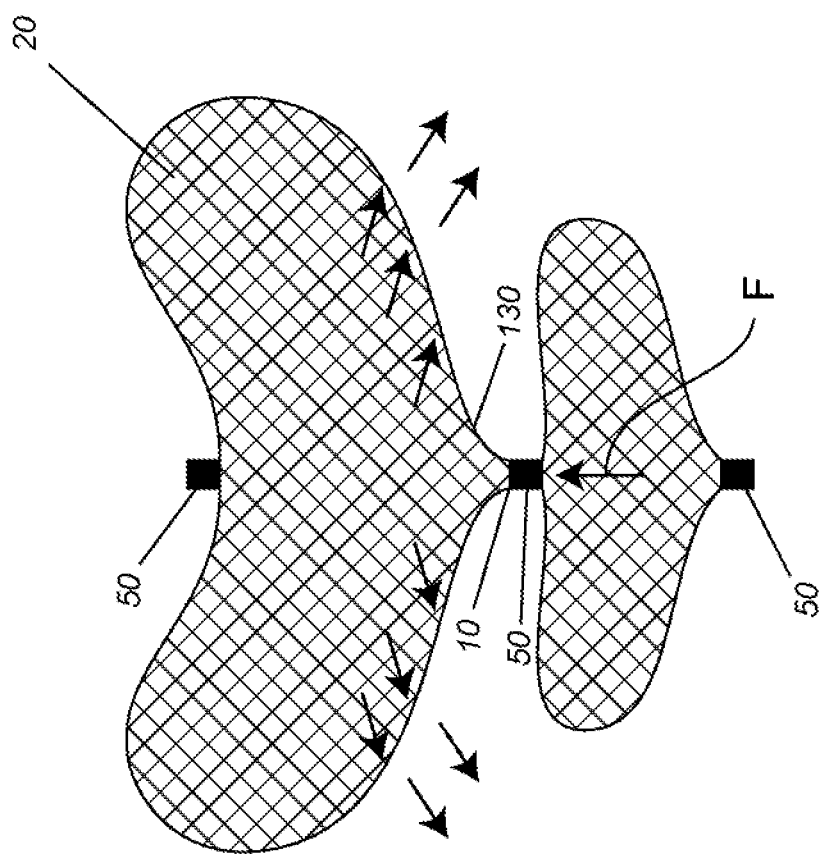
FIG. 9 illustrates a perspective view of an embodiment of an occlusion device disclosed herein having a series of two variably sized mesh carriages.

FIGS. 9 and 10 show embodiments of an occlusion device as disclosed herein. In such embodiments, the distal 20 carriage (top 20 carriage in FIGS. 9 & 10) expands into the 90 aneurysm and creates a stable structure for the variably sized, smaller subsequent 20 carriage to push against thereby stabilizing the device as it sits across (or within) the 100 aneurysm neck. In such a configuration, and in one embodiment, the hourglass-like 130 shape of the distal 20 carriage leading into the 10 pinch point and/or 50 marker located between the 20 carriages contributes to overall stability of the device. In another embodiment, the hourglass-like 130 shape of the distal 20 carriage is defined by its projection outward toward the subsequent 20 carriage rather than recessing into itself. FIGS. 9 and 10 show the distribution of forces with arrows. Force (F) distributes forces or pressure into the distal 20 carriage which embeds and secures the device stably into place within the 90 aneurysm. Like other variable configurations of the series of 20 carriages shown in FIG. 2, FIG. 10 shows that the diameter or 40 width (y) of the last 20 carriage to enter the 90 aneurysm will be larger than the 100 aneurysm neck which ensures this last 20 carriage remains secure (and is anchored) inside the 90 aneurysm so as to disrupt blood flow and ultimately create stasis.

Without wishing to be bound by theory, this configuration of a continuous compressible mesh structure divided into segments of axial 20 carriages triggers a mechanism of action believed to contribute to enhanced acute thrombogenicity of the device in animal studies. It is also believed that the localizing of a small volume of clot between the series of 20 carriage layers and compartments, which have a high surface area contribution from the wire strands, facilitates nucleating and stabilizing thrombus in an 90 aneurysm. This compartmentalization of the occlusion device in its deployed shape is an effective stabilizing or anchoring feature of the deployed device as blood applies pressure to the mesh structure distributed across or within the 100 neck of the aneurysm. Such a configuration also provides sufficient apposition of the compressible device against the 90 aneurysm wall or vessel wall for peripheral arterial or venous occlusion. The device disclosed herein provides sufficient mesh density to confer stasis acutely and the wire mesh/braid distribution remains relatively uniform in deployment.

In another embodiment of an occlusion device disclosed herein, the compressible axial mesh 20 carriages comprise a relatively uniform distribution of wire mesh strands or braids such as, without limitation, a 72 NiTi wire mesh strand braided configuration or a combination of 72 NiTi and CoCr wire mesh strand braided configuration. In other embodiments, the occlusion device comprises wire mesh strands or braids that range from 36 to 144 NiTi strand braided configuration.

Figure 5:
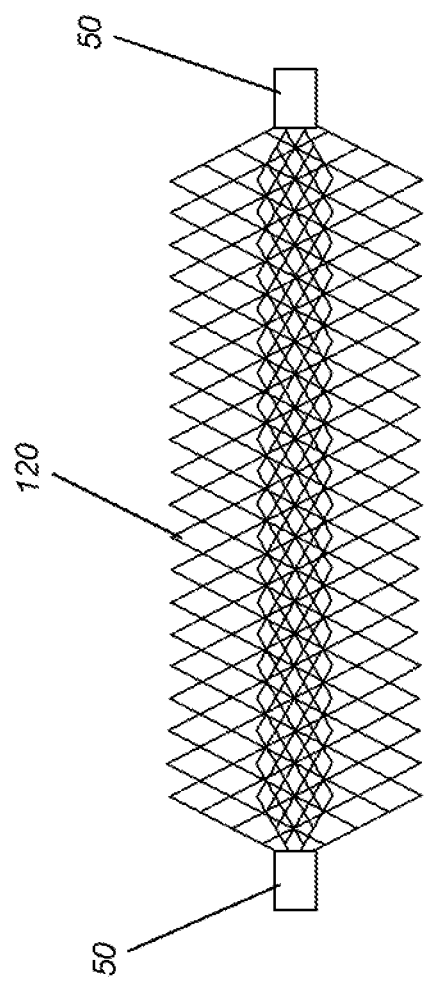
FIG. 5 illustrates a perspective view of an embodiment of an occlusion device disclosed herein having a mesh carriage comprising an inner coaxial mesh carriage.
Figure 6:
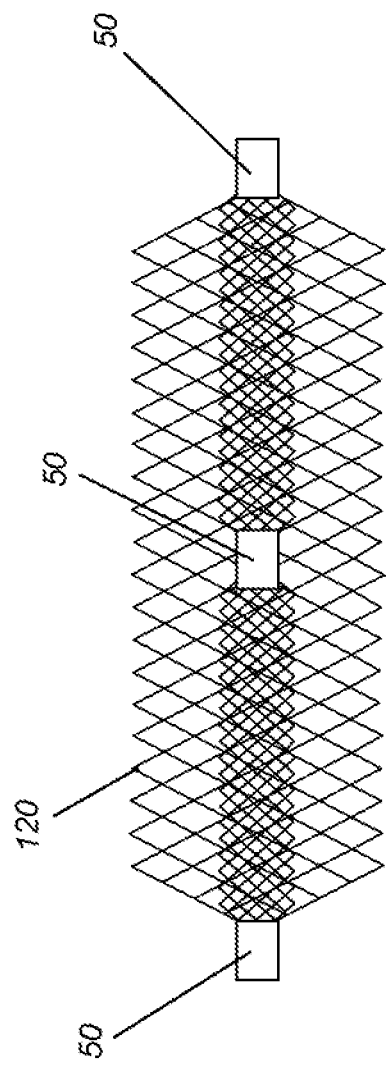
FIG. 6 illustrates a perspective view of an embodiment of an occlusion device disclosed herein having a mesh carriage comprising inner coaxial mesh carriages.

FIG. 5 shows a singular compressible axial mesh 20 carriage comprising a 120 coaxial inner mesh carriage. FIG. 6 shows a singular axial mesh 20 carriage comprising 120 coaxial inner mesh carriages. Such a 120 coaxial mesh inner or 120 coaxial mesh inner creates greater flow disruption and compartmentalization than an axial mesh 20 carriage without a 120 coaxial mesh inner carriage, thereby introducing stasis and thrombus stabilization. In another embodiment, the axial 20 carriage and the 120 coaxial carriage (or carriages) are constructed of dissimilar metal mesh. In a further embodiment, the dissimilar metal mesh creates a galvanic effect which can further enhance thrombus development. In another further embodiment, the dissimilar metal mesh can be comprised of one metal in one 20 carriage which possesses radiopaque properties relative to the metal in the other 20, 120 carriage and thus enhances visualization of the device. In such embodiments, braid mesh density can be the same or different in axial outer 20 carriages and 120 coaxial inner carriages and wires of the inner and outer mesh can have different numbers of strands and wire diameters. Such a 120 coaxial carriage or coaxial carriages are variable in dimension compared to the outer axial 20 carriage. For example, in one embodiment, a 120 coaxial carriage or carriages can range from about 5% to about 95% of the dimensions of the outer axial 20 carriage of which the 120 coaxial carriage or coaxial carriages is/are comprised within. FIG. 7 shows the 20 axial and 120 coaxial carriages loaded in the 70 catheter lumen and FIG. 8 shows electrolytic device deployment with an electrolytic detachable 60 pusher wire and the expansion of the 20, 120 carriages (outer and inner) exiting the 70 catheter tip.

In one embodiment, a 50 marker such as a ring encircles the 10 pinch points defining each end of each 20, 120 carriage of the continuous mesh structure. As such, the 50 marker of the occlusion device disclosed herein is a substantially solid collar or rigid member such as, without limitation a solid ring or band comprised of materials such as, without limitation, gold, platinum, stainless steel, and/or combinations thereof. In another embodiment, radiopaque materials such as, without limitation, gold, platinum, platinum/iridium alloy, and/or combinations thereof, can be used. Such a 50 marker provides positional visualization of the device during delivery and placement. The 50 markers are located on the occlusion device encircling 10 pinch points on each end of each 20, 120 carriage. In this manner, the 50 marker located at the proximal end of the proximal 20, 120 carriage is capable of resting above or within the 100 neck of an 90 aneurysm. The solidness of the 50 markers help confer stability of the device within the 90 aneurysm and prevents movement or the transfer of forces through the compressible mesh 20, 120 carriages thereby preventing misplacement or accidental movement of the device. The 50 markers are also configured with a junction to cooperate and release from/attach to a corresponding delivery means such as, without limitation, a delivery 70 catheter or 60 guide wire and/or pusher wire technologies. It also advantageously provides for full retrievability of the device disclosed herein.

In another embodiment, the substantially solid 50 marker comprises a radiopaque material (such as for example, without limitation, platinum, gold, platinum/iridium alloy, and/or combinations thereof) to facilitate visualization of the occlusion device under fluoroscopy during delivery, placement and/or deployment. The 50 marker comprises a proximal end and a distal end. Occlusion devices disclosed herein may be configured to incorporate the use of markers to influence shape, diameter, and/or curvature of the compressible 20, 120 carriages upon expansion during deployment. Additionally, the 50 marker may be designed in various shapes to influence the overall profile of the occlusion device having a series of mesh 20, 120 carriages to ensure a proper fit of the expanded/deployed occlusion device within the 90 aneurysm sac.

FIGS. 3, 7 and 8 show exemplary means for electrolytic delivery and/or deployment and/or detachment of the occlusion device disclosed herein through an artery and/or 110 vessel adjacent to the 90 aneurysm or body lumen. Electrolytic detachment means and methods such as U.S. Pat. No. 5,122,136 are well known in the art. In one embodiment, a coil-wound 60 core wire (or guide wire or pusher wire) of the 70 catheter (or micro-catheter) is attached inside the 50 marker at its most distal end to the occlusion device disclosed herein (as shown in FIGS. 3, 7 and 8). The coil wind maintains a constant diameter ($\phi$) so as not to impact upon flexibility or stiffness of the delivery 70 catheter or micro-catheter or 60 guide wire. In certain embodiments, FEP (Fluorinated Ethylene Propylene) heat shrink tubing encases the coil-wound portion of the core wire. Numerous readily available and well known attachment techniques in the medical device arts can be used to attach the distal end of the core wire inside the marker and to the occlusion device or implant. Such attachment techniques include, without limitation, adhesives, laser melting, laser tack, spot, and/or continuous welding. In one embodiment, an adhesive is used to attach the distal end of the core wire inside the marker. In a further embodiment, the adhesive is an epoxy material which is cured or hardened through the application of heat or UV (ultra-violet) radiation. In an even further embodiment, the epoxy is a thermal cured, two-part epoxy such as EPO-TEK® 353ND-4 available from Epoxy Technology, Inc., 14 Fortune Drive, Billerica, Mass. Such an adhesive or epoxy material encapsulates the junction of the core wire inside the 50 marker and increases its mechanical stability.

In another embodiment, during and/or after deployment of the device, the coil-wound 60 core wire detaches the occlusion device disclosed herein at an 80 electrolytic detachment site (or zone) on the 60 core wire itself in such a manner so that the 60 core wire is severed and/or dissolved through electrolytic action at the base of the 50 marker. Such action then releases and/or places the occlusion device into an 90 aneurysm or vessel to be treated.

In certain embodiments, the compressible mesh structure of the occlusion device disclosed herein can be filled with an embolic material to promote clotting and closure of the 90 aneurysm.

In other embodiments, the occlusion device disclosed herein may further incorporate adjunctive elements and/or members such as coiling techniques, framing coils, embolic agents, additional markers, polymers, resorbent polymers and/or a combination thereof.

Resilient and compressible mesh materials for design and/or manufacture of occlusion devices are readily available and well known by those skilled in the relevant art. As such, resilient and compressible mesh materials range from a wide variety of available materials such as, without limitation, nickel titanium (nitinol or otherwise known as NiTi), stainless steel, polymers, and/or combinations thereof. Exemplary known biomedical polymeric families include, without limitation, polymers such as polyphosphazenes, polyanhydrides, polyacetals, poly(ortho esters), polyphosphoesters, polycaprolactones, polyurethanes, polylactides, polycarbonates, polyamides, and/or a combination thereof. (See, e.g., J. Polym Sci B Polym Phys. Author manuscript; available in PMC 2012 Jun. 15.)

In one exemplary embodiment, the resilient and compressible mesh material is formed of woven strands of polymer material, such as, without limitation, nylon, polypropylene or polyester. The polymer strands can be filled with a radiopaque material which allows the physician treating the aneurysm to fluoroscopically visualize the location of the device within the vasculature. Radiopaque filler materials preferably include bismuth trioxide, tungsten, titanium dioxide or barium sulfate, or radiopaque dyes such as iodine. The resilient and compressible mesh material can be formed by strands of radiopaque material. The radiopaque strands allow the physician and/or radiologist to fluoroscopically visualize the location of the mesh, without the use of filled polymer materials. Such radiopaque strands may be formed with materials such as, without limitation, gold, platinum, a platinum/iridium alloy, and/or a combination thereof. In one embodiment, the resilient mesh material is constructed of 10%-45% platinum core NiTi. In another embodiment, the resilient mesh material is constructed of 10% platinum core NiTi, 15% platinum core NiTi, 20% platinum core NiTi, or 45% platinum core 10% platinum core NiTi construction is sufficient to provide a ghost image of the occlusion device under x-ray.

Such constructed combination wires or composite wires having a radiopaque core and non-radiopaque outer layer or casing are readily available and well known in the medical device and metallic arts as DFT® (drawn-filled-tube) wires, cables or ribbons. DFT® wire is a metal-to-metal composite constructed to combine the desired physical and mechanical attributes of two or more materials into a single wire. By placing the more radiopaque, but more ductile material in the core of the wire, the NiTi outer layer is able to provide the resulting composite wire with similar mechanical properties of a 100% NiTi wire. DFT® wires are available from Fort Wayne Metals Corp., Fort Wayne, Ind., U.S.A. See also, for example, the journal article entitled Biocompatible Wire by Schaffer in Advanced Materials & Processes, October 2002, pages 51-54, incorporated herein by reference.

Where the compressible mesh structure is formed of radiopaque metal strands, the strands may be covered with a polymer coating or extrusion. The coating or extrusion over the radiopaque wire strands provides fluoroscopic visualization but also increases the resistance of the strands to bending fatigue and may also increase lubricity of the strands. The polymer coating or extrusion, in one embodiment, is coated or treated with an agent which tends to resist clotting, such as heparin. Such clot resistant coatings are generally known. The polymer coating or extrusion can be any suitable extrudable polymer, or any polymer that can be applied in a thin coating, such as Teflon® or polyurethane.

In yet another embodiment, the strands of the compressible mesh structure are formed using both metal and polymer braided strands. Combining the metal strands with the polymer strands into a braid changes the flexibility characteristics of mesh. The force required to deploy and/or collapse such a mesh portion is significantly reduced over that required for a mesh portion that includes only metal mesh strands. However, the radiopaque characteristics of the mesh for fluoroscopic visualization are retained. Metal strands forming such a device includes, without limitation, stainless steel, gold, platinum, platinum/iridium, nitinol, and/or combinations thereof. Polymer strands forming the device can include nylon, polypropylene, polyester, Teflon®, and/or combinations thereof. Further, polymer strands of the mesh material can be chemically modified to make them radiopaque with known techniques such as, without limitation, by using gold deposition onto the polymer strands, or by using ion beam plasma deposition of suitable metal ions onto the polymer strands.

The compressible mesh structure can also be formed with filaments or strands of varying diameter and/or varying flexibility. For example, wire diameters for use in the occlusion device disclosed herein range from about 0.0075 inches up to about 0.005 inches. By varying the size or flexibility of the polymer strands, the flexibility characteristics of the mesh, upon deployment, can also be varied. By varying the flexibility characteristics, both the deployed (compressed) and delivery (constrained) configuration of the resilient and compressible mesh structure can be varied or changed to substantially any desired shape.

Not only can the mesh be formed of both polymer strands or filaments and metal strands or filaments, but it can be formed using filaments of different polymer materials. For example, different polymer materials having different flexibility characteristics can be used in forming the mesh. This alters the flexibility characteristics to change the resultant configuration of the mesh structure in both the deployed and the collapsed positions. Such biomedical polymers are readily known and available in the art and can be derived from polymeric families such as, without limitation, polyphosphazenes, polyanhydrides, polyacetals, poly (ortho esters), polyphosphoesters, polycaprolactones, polyurethanes, polylactides, polycarbonates, polyamides, and/or a combination thereof.

Compressible mesh materials suitable for use within the mesh carriages may take the form of a flat woven sheet, knitted sheet, or a laser cut wire mesh. In general, the material should include two or more sets of substantially parallel strands, with one set of parallel strands being at a pitch of between 45 degrees and 135 degrees with respect to the other set of parallel strands. In some embodiments, the two sets of parallel strands forming the mesh material are substantially perpendicular to each other. The pitch and general construction of the mesh material may be optimized to meet the performance needs of the occlusion device.

The wire strands of the metal fabric used in the occlusion device disclosed herein should be formed of a material which is both resilient and compressible and can be heat-treated to substantially set a desired shape. Materials which are believed to be suitable for this purpose include a cobalt-based low thermal expansion alloy referred to in the field of occlusion devices as Elgiloy®, nickel-based high-temperature high-strength "superalloys" commercially available from Haynes International under the trade name Hastelloy®, nickel-based heat treatable alloys sold under the name Incoloy® by International Nickel, and a number of different grades of stainless steel. The important factor in choosing a suitable material for the wires is that the wires retain a suitable amount of the deformation induced by the molding surface (or shape memory, as described below) when subjected to a predetermined heat treatment.

One class of materials which meet these qualifications are so-called shape memory alloys. Such alloys tend to have a temperature induced phase change which will cause the material to have a preferred configuration which can be fixed by heating the material above a certain transition temperature to induce a change in the phase of the material. When the alloy is cooled, the alloy will "remember" the shape it was in during the heat treatment and will tend to assume that same and/or similar configuration unless constrained from doing so.

One particular shape memory alloy for use in the occlusion device disclosed herein is nitinol, an approximately stoichiometric alloy of nickel and titanium, which may also include other minor amounts of other metals to achieve desired properties. NiTi alloys such as nitinol, including appropriate compositions and handling requirements, are well known in the art and such alloys need not be discussed in detail here. For example, U.S. Pat. Nos. 5,067,489 and 4,991,602, the teachings of which are incorporated herein by reference, discuss the use of shape memory NiTi alloys in guide wire-based technologies. Such NiTi alloys are preferred, at least in part, because they are commercially available and more is known about handling such alloys than other known shape memory alloys. NiTi alloys are also very elastic. Indeed, they are said to be known as "superelastic" or "pseudoelastic." This elasticity will help an occlusion device as disclosed herein return to prior expanded configuration for deployment thereof.

The wire strands can comprise a standard monofilament of the selected material, i.e., a standard wire stock may be used. In some embodiments, 72 wire strands and/or 72 strand braid configuration is used. In other embodiments, the occlusion device comprises wire mesh strands or braids that range from 36 to 144 NiTi strand braided configurations. If so desired, though, the individual wire strands may be formed from "cables" made up of a plurality of individual wires. For example, cables formed of metal wires where several wires are helically wrapped about a central wire are commercially available and NiTi cables having an outer diameter of 0.003 inches or less can be purchased. One advantage of certain cables is that they tend to be "softer" than the monofilament wires having the same diameter and formed of same material. Additionally, the use of a cable can increase the effective surface area of the wire strand, which will tend to promote thrombosis.

An occlusion device disclosed herein is configured with a continuous mesh structure having a series of compressible axial 20 carriages (defined by 10 pinch points) having a mesh density sufficient for functioning in such a manner as an endothelial cell scaffold layers or compartments filling a vessel or body lumen or 90 aneurysm and thereby reducing blood flow by about 60% to trigger clot formation and/or healing of the 90 aneurysm and/or ultimate stasis. For the purposes of the occlusion device disclosed herein, the terminology "mesh density" means the level of porosity or the ratio of metal to open area of the mesh structure. Mesh density relates to the number and size of the openings or pores of the mesh and by the extent that the pores are open or closed in situations where opening or pore openness varies between delivery and deployment. Generally, a high mesh density region of a resilient mesh material has approximately about 40% or more metal area and about 60% or less open area.

In some embodiments, the compressible mesh structure may be formed uniformly of the same material; however, such material may have different knitted, stitched, braided, and/or cut construction.

In other embodiments, the implantable occlusion device disclosed herein can be used for the process of peripheral vascular embolization (a process well known in the art and known to involve the shutdown of blood flow distal to a specified vascular point), for example, in the treatment and/or amelioration of peripheral arterial or venous pathologies and/or any related pathologies requiring vessel occlusion for the treatment thereof.

The occlusion device disclosed herein may incorporate reasonable design parameters, features, modifications, advantages, and variations that are readily apparent to those skilled in the art in the field of occlusion devices.

EXAMPLES

A study protocol with respect to the occlusion device disclosed herein and justification for animal use will be reviewed and approved by the Institutional Animal Care and Use Committee (IACUC) at ISIS Services and the procedures carried out under veterinarian supervision.

The rabbit elastase aneurysm model is a well-accepted and art-recognized model for testing novel neurointerventional devices and has been the subject of a number of clinical publications regarding efficacy and similarity to human response. (See, e.g., Altes et al. Creation of Saccular Aneurysms in the Rabbit: A Model Suitable for Testing Endovascular Devices. AJR 2000; 174: 349-354.) It therefore is readily accepted by the regulatory agencies as an appropriate test model. The model's coagulation system is highly similar to that of humans. In addition, the model has advantageous anatomical aspects in that the diameters of the rabbits' extra-cranial carotid arteries are highly similar to the diameter of extra-cranial carotid arteries in humans. Moreover, elastase-induced aneurysms have been shown to behave in a histologically similar manner as human aneurysms.

A number of embodiments of the invention have been described. Without departing from the scope and spirit of the occlusion device disclosed herein, reasonable features, modifications, advantages, and design variations of the claimed apparatus will become readily apparent to those skilled in the art by following the guidelines set forth in the preceding detailed description and embodiments. Accordingly, other embodiments are within the scope of the following claims.

What is claimed is:

1. An occlusion device for implantation into a body lumen or aneurysm comprising a continuous compressible mesh structure comprising axial mesh carriages configured end to end, wherein each end of each carriage is a pinch point in the continuous mesh structure wherein a radiopaque marker encircles at least one pinch point, and wherein each carriage has a uniform width (x) and length (y) and wherein at least one axial carriage comprises an inner coaxial mesh carriage or inner coaxial mesh carriages and wherein the inner coaxial mesh carriage or the inner coaxial mesh carriages is dissimilar material to a corresponding outer axial mesh carriage.

2. The occlusion device of claim 1, wherein the number of axial carriages is equal to (n) and (n) is selected from the group consisting of two axial carriages, three axial carriages, four axial carriages, and five axial carriages.

3. The occlusion device of claim 1, wherein the inner coaxial mesh carriages are two inner coaxial mesh carriages, or three inner coaxial mesh carriages.

4. The occlusion device of claim 1, wherein the continuous mesh structure expands in a deployed shape and fills the body lumen or aneurysm, whereby the deployed shape compresses its axial length (x) of each axial carriage to about 5% to about 50% of its axial length in free air.

5. The occlusion device of claim 1 including a delivery system.

6. The occlusion device of claim 5 wherein the delivery system is a microcatheter, catheter, guide wire or pusher wire.

7. An occlusion device for implantation into a body lumen or aneurysm comprising a continuous compressible mesh structure comprising axial mesh carriages configured end to end, wherein each end of each carriage is a pinch point in the continuous mesh structure wherein a radiopaque marker encircles at least one pinch point, and wherein each carriage has a uniform width (x) and length (y), wherein at least one axial carriage comprises an inner coaxial mesh carriage or inner coaxial mesh carriages and wherein the inner coaxial mesh carriage or the inner coaxial mesh carriages has dissimilar mesh density to a corresponding outer axial mesh carriage.

8. The occlusion device of claim 7, wherein the number of axial carriages is equal to (n) and (n) is selected from the group consisting of two axial carriages, three axial carriages, four axial carriages, and five axial carriages.

9. The occlusion device of claim 8, wherein the inner coaxial mesh carriages are two inner coaxial mesh carriages, or three inner coaxial mesh carriages).

10. The occlusion device of claim 7 wherein the continuous mesh structure expands in a deployed shape and fills the body lumen or aneurysm, whereby the deployed shape compresses its axial length (x) of each axial carriage to about 5% to about 50% of its axial length in free air.

11. The occlusion device of claim 7 including a delivery system.

12. The occlusion device of claim 6 wherein the delivery system is a microcatheter, catheter, guide wire or pusher wire.

* * * * *

UNITED STATES PATENT AND TRADEMARK OFFICE
CERTIFICATE OF CORRECTION

PATENT NO. : 11,471,162 B2
APPLICATION NO. : 16/407957
DATED : October 18, 2022
INVENTOR(S) : Stephen Griffin It is certified that error appears in the above-identified patent and that said Letters Patent is hereby corrected as shown below:

In the Claims

Column 16, Line 37, Claim 9, delete "carriages)." and insert --carriages.--.

Signed and Sealed this
Nineteenth Day of December, 2023

*Katherine Kelly Vidal*

Katherine Kelly Vidal
*Director of the United States Patent and Trademark Office*